United States Patent
Gabelberger et al.

(10) Patent No.: US 8,652,174 B2
(45) Date of Patent: Feb. 18, 2014

(54) EXPANDABLE INTERSPINOUS PROCESS SPACER

(75) Inventors: Josef Gabelberger, West Chester, PA (US); Zoher Bootwala, Wilmington, DE (US); Justin Coppes, Downington, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/544,320

(22) Filed: Jul. 9, 2012

(65) Prior Publication Data

US 2012/0277796 A1    Nov. 1, 2012

Related U.S. Application Data

(62) Division of application No. 12/645,289, filed on Dec. 22, 2009, now Pat. No. 8,216,278.

(60) Provisional application No. 61/139,794, filed on Dec. 22, 2008.

(51) Int. Cl.
*A61B 17/70* (2006.01)
(52) U.S. Cl.
USPC .......................................................... 606/249
(58) Field of Classification Search
USPC ................................................. 606/248, 249
See application file for complete search history.

(56) References Cited

U.S. PATENT DOCUMENTS

| | | | |
|---|---|---|---|
| 2,677,369 A | 5/1954 | Knowles | |
| 3,648,691 A | 3/1972 | Lumb et al. | |
| 5,059,193 A | 10/1991 | Kuslich | |
| 5,496,318 A | 3/1996 | Howland et al. | |
| 5,653,763 A | 8/1997 | Errico et al. | |
| 6,080,193 A | 6/2000 | Hochshuler et al. | |

(Continued)

FOREIGN PATENT DOCUMENTS

| | | |
|---|---|---|
| FR | 2625097 | 6/1989 |
| FR | 2700941 | 8/1994 |

(Continued)

OTHER PUBLICATIONS

Benzel, et al., "Posterior cervical interspinous compression wiring and fusion for mid to low cervical spinal injuries," J. Neurosurg., 1989, pp. 893-899, vol. 70.

(Continued)

*Primary Examiner* — Ellen C Hammond
(74) *Attorney, Agent, or Firm* — Meunier Carlin & Curfman, LLC

(57) ABSTRACT

An expandable interspinous process spacer implant for insertion and/or implantation between a spinous process of a superior vertebral body and a spinous process of an inferior vertebral body, the implant comprising multiple pairs of legs joined in a scissor-like fashion and pivotally coupled to each other by one or more pins, where each leg has multiple slots along its longitudinal axis. The implant further may include a pair of bearing surfaces coupled between the legs via cross pins and a first plate and second plate each of which is coupled to a pair of roller pins disposed between a pair of slots on the legs where rotation of a fastener in the fastener holes of the first and second plate results in the first plate and the second plate being drawn toward each other causing the expansion of the height of the implant.

21 Claims, 17 Drawing Sheets

(56) References Cited

U.S. PATENT DOCUMENTS

| | | | |
|---|---|---|---|
| 6,126,689 A | 10/2000 | Brett | |
| 6,235,030 B1 | 5/2001 | Zucherman et al. | |
| 6,332,882 B1 | 12/2001 | Zucherman et al. | |
| 6,332,883 B1 | 12/2001 | Zucherman et al. | |
| 6,419,676 B1 | 7/2002 | Zucherman et al. | |
| 6,451,019 B1 | 9/2002 | Zucherman et al. | |
| 6,500,177 B1 | 12/2002 | Martinelli et al. | |
| 6,652,527 B2 | 11/2003 | Zucherman et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,733,534 B2 | 5/2004 | Sherman | |
| 6,761,720 B1 | 7/2004 | Senegas | |
| 6,946,000 B2 | 9/2005 | Senegas et al. | |
| 7,029,473 B2 | 4/2006 | Zucherman et al. | |
| 7,070,598 B2 | 7/2006 | Lim et al. | |
| 7,087,055 B2 | 8/2006 | Lim et al. | |
| 7,097,648 B1 | 8/2006 | Globerman et al. | |
| 7,201,751 B2 | 4/2007 | Zucherman et al. | |
| 7,238,204 B2 | 7/2007 | Le Couedic et al. | |
| 7,335,203 B2 | 2/2008 | Winslow et al. | |
| 8,216,278 B2 * | 7/2012 | Gabelberger et al. | 606/249 |
| 2004/0220568 A1 | 11/2004 | Zucherman et al. | |
| 2005/0055031 A1 | 3/2005 | Lim | |
| 2005/0143738 A1 | 6/2005 | Zucherman et al. | |
| 2005/0182416 A1 | 8/2005 | Lim et al. | |
| 2005/0203512 A1 | 9/2005 | Hawkins et al. | |
| 2005/0203624 A1 | 9/2005 | Serhan et al. | |
| 2005/0209603 A1 | 9/2005 | Zucherman et al. | |
| 2005/0228383 A1 | 10/2005 | Zucherman et al. | |
| 2005/0261768 A1 | 11/2005 | Trieu | |
| 2006/0058876 A1 | 3/2006 | McKinley | |
| 2006/0084988 A1 | 4/2006 | Kim | |
| 2006/0085069 A1 | 4/2006 | Kim | |
| 2006/0085070 A1 | 4/2006 | Kim | |
| 2006/0122701 A1 | 6/2006 | Kiester | |
| 2006/0184247 A1 | 8/2006 | Edidin et al. | |
| 2006/0184248 A1 | 8/2006 | Edidin et al. | |
| 2006/0241601 A1 | 10/2006 | Trautwein et al. | |
| 2006/0264938 A1 | 11/2006 | Zucherman et al. | |
| 2006/0271049 A1 | 11/2006 | Zucherman et al. | |
| 2007/0010813 A1 | 1/2007 | Zucherman et al. | |
| 2007/0032790 A1 | 2/2007 | Aschmann et al. | |
| 2007/0043361 A1 | 2/2007 | Malandain et al. | |
| 2007/0043362 A1 | 2/2007 | Malandain et al. | |
| 2007/0043363 A1 | 2/2007 | Malandain et al. | |
| 2007/0049934 A1 | 3/2007 | Edidin et al. | |
| 2007/0049935 A1 | 3/2007 | Edidin et al. | |
| 2007/0055237 A1 | 3/2007 | Edidin et al. | |
| 2007/0073398 A1 | 3/2007 | Fabian et al. | |
| 2007/0093830 A1 | 4/2007 | Zucherman et al. | |
| 2007/0173832 A1 | 7/2007 | Tebbe et al. | |
| 2007/0203493 A1 | 8/2007 | Zucherman et al. | |
| 2007/0203497 A1 | 8/2007 | Zucherman et al. | |
| 2007/0203501 A1 | 8/2007 | Zucherman et al. | |
| 2007/0208347 A1 | 9/2007 | Zucherman et al. | |
| 2007/0219552 A1 | 9/2007 | Zucherman et al. | |
| 2007/0225706 A1 | 9/2007 | Clark et al. | |
| 2007/0225724 A1 | 9/2007 | Edmond | |
| 2007/0233076 A1 | 10/2007 | Trieu | |
| 2008/0045958 A1 | 2/2008 | Zucherman et al. | |
| 2008/0046085 A1 | 2/2008 | Zucherman et al. | |
| 2008/0108990 A1 | 5/2008 | Mitchell et al. | |

FOREIGN PATENT DOCUMENTS

| | | |
|---|---|---|
| FR | 2717675 | 9/1995 |
| GB | 2 436 292 | 9/2007 |
| JP | 9075381 | 3/1997 |
| WO | 94/26192 | 11/1994 |
| WO | 95/25485 | 9/1995 |
| WO | 2005/009300 | 2/2005 |
| WO | 2006045094 | 4/2006 |
| WO | 2006/064356 | 6/2006 |
| WO | 2006113080 | 10/2006 |

OTHER PUBLICATIONS

Caserta, et al., "Elastic stabilization alone or combined with rigid fusion in spinal surgery: a biomechanical study and clinical experience based on 82 cases," Eur. Spine J., Oct. 2002, pp. S192-S197, vol. 11, Suppl. 2.

Christie, et al., "Dynamic Interspinous Process Technology," Spine, 2005, pp. S73-S78, vol. 30, No. 16S.

Cousin Biotech, "Analysis of Clinical Experience with a Posterior Shock Absorbing Implant," date unknown pp. 2-9.

Cousin Biotech, Dispositif Intervertebral Amortissant, Jun. 1998, pp. 1-4.

Cousin Biotech, Technique Operatoire De La Prothese DIAM, date unknown, Annexe 1, pp. 1-8.

Dickman, et al., "The interspinous method of posterior atlantoaxial arthrodesis," J. Neurosurg., 1991, pp. 190-198, vol. 74.

Dispositivo Intervertebrale Ammortizzante "DIAM", date unknown, p. 1.

Dubois et al., " Dynamic Neutralization: A New Concept for Restabilization of the Spine," Lumbar Segmental Instability, Szpalski et al., eds., 1999, pp. 233-240, Lippincott Williams & Wilkins, Philadelphia, Pennsylvania.

Ebara, et al., "Intraoperative Measurement of Lumbar Spinal Instability," Spine, 1992, pp. S44-S50, vol. 17, No. 3S.

Fassio, et al., "Treatment of Degenerative Lumbar Spinal Instability L4-L5 by Interspinous Ligamentoplasty," Rachis, Dec. 1991, pp. 465-473, vol. 3, No. 6.

Fassio, "Mise Au Point Sur La Ligamentoplastie Inter-Epineuse Lombaire Dans Les Instabilites," Maitrise Orthopedique, Jul. 1993, pp. 18, No. 25.

Garner, et al., "Development and preclinical testing of a new tension-band device for the spine: the Loop System," Eur. Spine J., Aug. 7, 2002, pp. S186-S191, vol. 11, Suppl. 2.

Guang, et al., "Interspinous Process Segmental Instrumentation with Bone-Button-Wire for Correction of Scoliosis," Chinese Medical J., 1990, pp. 721-725, vol. 103.

Guizzardi, et al., "The use of DIAM (Interspinous Stress-Breaker Device) in the Prevention of Chronic Low Back Pain in Young Patients Operated on for Large Dimension Lumbar Disc Herniation," 12th Eur. Congress of Neurosurgery (EANS), Sep. 7-12, 2003, pp. 835-839, Lisbon, Portugal.

Hambly, et al., "Tension Band Wiring-Bone Grafting for Spondylolysis and Spondylolisthesis," Spine, 1989, pp. 455-460, vol. 14, No. 4.

Kiwerski, "Rehabilitation of patients with thoracic spine injury treated by spring alloplasty," Int. J. Rehab. Research, 1983, pp. 469-474, vol. 6, No. 4.

Laudet, et al., "Comportement Bio-Mecanique D'Un Ressort Inter-Apophysaire Vertebral Posterieur Analyse Experimentale Du Comportement Discal En Compression Et En Flexion/Extenstion," Rachis, 1993, vol. 5, No. 2.

Lindsey, et al., "The Effects of an Interspinous Implant on the Kinematics of the Instrumented and Adjacent Levels in the Lumbar Spine," Spine, 2003, pp. 2192-2197, vol. 28, No. 19.

Mah, et al., "Threaded K-Wire Spinous Process Fixation of the Axis for Modified Gallie Fusion in Children and Adolescents," Journal of Pediatric Orthopaedics, 1989, pp. 675-679, vol. 9, No. 6.

Mariottini, et al., "Preliminary results of a soft novel lumbar intervertebral prothesis (DIAM) in the degenerative spinal pathology," Acta Neurochirurgica, Advanced Peripheral Nerve Surgery and Minimal Invasive Spinal Surgery, Alexandre, et al., eds., 2005, pp. 129-131, Suppl. 92.

McDonnell, et al., "Posterior Atlantoaxial Fusion: Indications and Techniques," Techniques in Spinal Fusion and Stabilization, Hitchon et al., eds., 1995 pp. 92-106, Ch. 9 Thieme New York.

Muller, "Restauration dynamique de la stabilite rachidienne," Tire de la Sulzer Technical Review, Jan. 1999, Sulzer Management Ltd, Winterthur, Switzerland.

(56) References Cited

OTHER PUBLICATIONS

Minns, et al., "Preliminary Design and Experimental Studies of a Novel Soft Implant for Correcting Sagittal Plane Instability in the Lumbar Spine," Spine, 1997, pp. 1819-1825, vol. 22 No. 16.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini, et al., "Analisi Di Un'Esperienza Clinica Con Un Impianto Posteriore Ammortizzante," S.O.T.I.M.I. Societa di Ortopedia e Traumatologia dell'Italia Meridionale e Insulare 90 Congresso, Jun. 21-23, 2001, Paestum.

Petrini,et al., "Stabilizzazione Elastica," Patologia Degenerativa del Rachide Lombare, Oct. 5-6, 2001., Rimini.

Pupin, et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary, et al., "Cervical Spina Stabilization with Flexible, Multistrand Cable System," Techniques in Spinal Fusion and Stabilization, Hitchon et al., eds., 1995, pp. 79-81, Ch. 7, Thieme, New York.

Richards, et al., "The Treatment Mechanism of an Interspinous Process Implant for Lumbar Neurogenic Intermittent Claudication," Spine, 2005, pp. 744-749, vol. 30, No. 7.

Scarfo, "Instability/Stenosis: Holistic Approach for Less Invasive Surgery," date unknown, University of Siena, Siena, Italy.

Schiavone, et al., "The use of disc assistance prostheses (DIAM) in degenerative lumbar pathology: Indications Tecchnique, Results," Italian J. Spinal Disorders, 2003, pp. 213-220, vol. 3, No. 2.

Schlegel, et al, "The Role of Distraction in Improving the Space Available in the Lumbar Stenotic Canal and Foramen," Spine, 1994, pp. 2041-2047, vol. 19, No. 18.

Senegas, "Mechanical supplementation by non-rigid fixation in degenerative intervertebral lumbar segments: the Wallis system," Eur. Spine J., 2002, pp. S164-S169, vol. 11, Suppl. 2).

Senegas, et al., "Stabilisation lombaire souple," Instabilites Vertebrales Lombaires, Gastambide, ed., 1995, pp. 122-132, Expansion Scientifique Francaise, Paris, France.

Senegas, "La Ligamentoplastie Inter Vertebrale Lombaire, Alternative a L' Arthrodese," La Revue de Medecine Orthopedique, Jun. 1990, pp. 33-35, No. 20.

Senegas, "La Ligamentoplastie Intervertebrale, Alternative a L'Arthrodese Dans Le Traitement Des Instabilites Degeneratives," Acta Othopaedica Belgica, 1991, pp. 221-226, vol. 57, Suppl. I.

Senegas, "Recontre," Maitrise Orhtopedique, May 1995, pp. 1-3, No. 44.

Senegas, et al., "Le recalibrage du canal lombaire, alternative a la laminectomie dans le traitement des stenoses du canallombaire," Revue de Chirurgie Orthopedique, 1988, pp. 15-22.

Serharn, et al., "Spinal Implants: Past, Present, and Future," 19th International Conference IEEE/EMBS Conference, Oct. 30-Nov. 2, 1997, pp. 2636-2639.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—modified CAD geometry and meshing," date unknown.

Taylor, et al., "Technichal and Anatomical Considerations for the Placement of a Posterior Interspinous Stabilizer" Lumbar Spine, pp. 466-475.

Taylor, et al, "Technical and Anatomical Consideration for the Placement of a Posterior Interspinous Stabilizer", Medtronic, 2004, pp. 3-11.

Taylor, "Posterior Dynamic Stabilization using the DIAM (Device for Intervertebral Assisted Motion)".

Taylor, et al., "Analyse d'une experience clinique d'un implant posterieur amortissant, "Rachis Revue de Pathologie Vertebrale, Oct./Nov. 1999, vol. 11, No. 4-5, Gieda Inter Rachis.

Taylor, et al., "Biomechanical requirements for the posterior control of the centers of rotation.", Swiss Spine Institute International Symposium: Progress in Spinal Fixation, Jun. 21, 2002, pp. 1-2, Swiss Spine Institute, Berne, Switzerland.

Taylor, "Non-Fusion-Technologies of the posterior column: A new posterior shock absorber," International Symposium on Intervertebral Disc Replacement and Non-Fusion-Technology, May 3-5, 2001, Spine Arthroplasty.

Taylor, et al., "Surgical Requirement for the Posterior Control of the Rotational Centers," date unknown.

Taylor, "Presentation a un an d'un dispositif amortissant d' assistance discale," 5emes journees Avances & Controverses en pathologie rachidienne, Oct. 1-2, 1998, Faculte Libre de Medecine de Lille.

Technica Operatoria Per IL Posizionamento Della Protesi DIAM, date unknown, pp. 1-3.

The Posterior Intervertebral Implant of Professor J. Senegas, date unknown.

Vangilder, "Interspinolls, Laminar, and Facet Posterior Cervical Bone Fusions," Techniques in Spinal Fusion and Stabilization, Hitchon et al., eds., 1995. pp. 135-146, Ch. 13, Thieme, New York.

Voydeville, et al., "Experimental lumbar instability and artificial ligament," Eur. J. Orthop. Surg. Traumatol, 2000, pp. 167-176, vol. 10.

Voydeville, et al., "Lumbar Instability Treated by Intervertebral Ligamentoplasty with Smooth Wedges," Orthopedie Traumatologie, 1992, pp. 259-264, vol. 2, No. 4.

Wallis Operative Technique: Surgical Procedure for Treatment of Degenerative Disc Disease (DDD) of Lumbar Spine, date unknown, pp. 1-24, Spine Next, an Abbott Laboratories Company, Bordeaux, France.

Wiltse, et al., "The Treatment of Spinal Stenosis," Clinical Orthopaedics and Related Research, Urist, ed., Mar.-Apr. 1976, pp. 83-91, No. 115.

Wisneski, et al. "Decompressive Surgery for Lumbar Spinal Stenosis," Seminars in Spine Surgery, Wiesel, ed., Jun. 1994, pp. 116-123, vol. 6, No. 2.

Zucherman, et al., "Clinical Efficacy of Spinal Instrumentation in Lumbar Degenerative Disc Disease" Spine Jul. 1992. pp. 834-837 vol. 17 No. 7.

International Search Report and Written Opinion issued Jun. 29, 2011 in PCT/US2009/069308.

\* cited by examiner

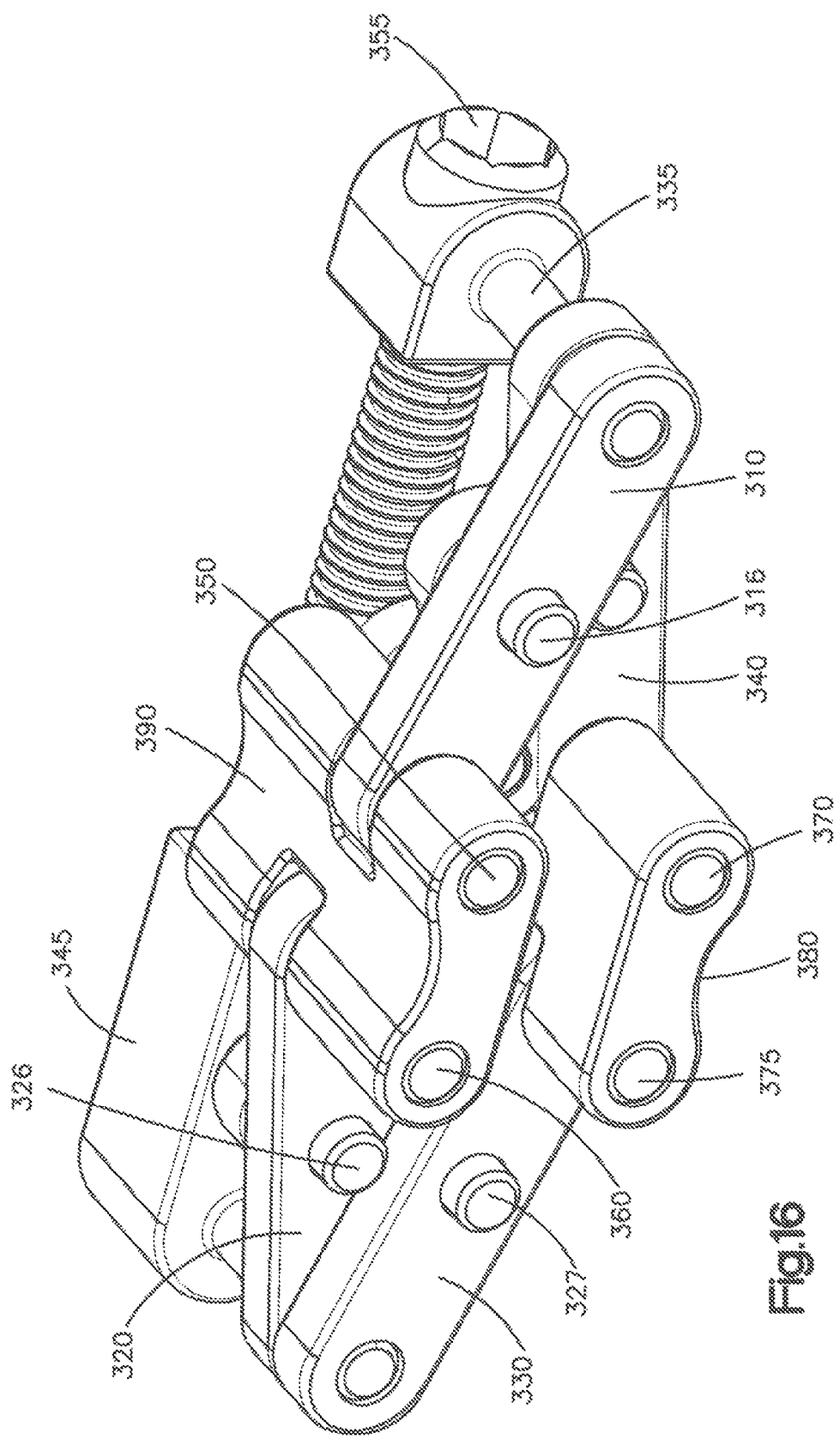

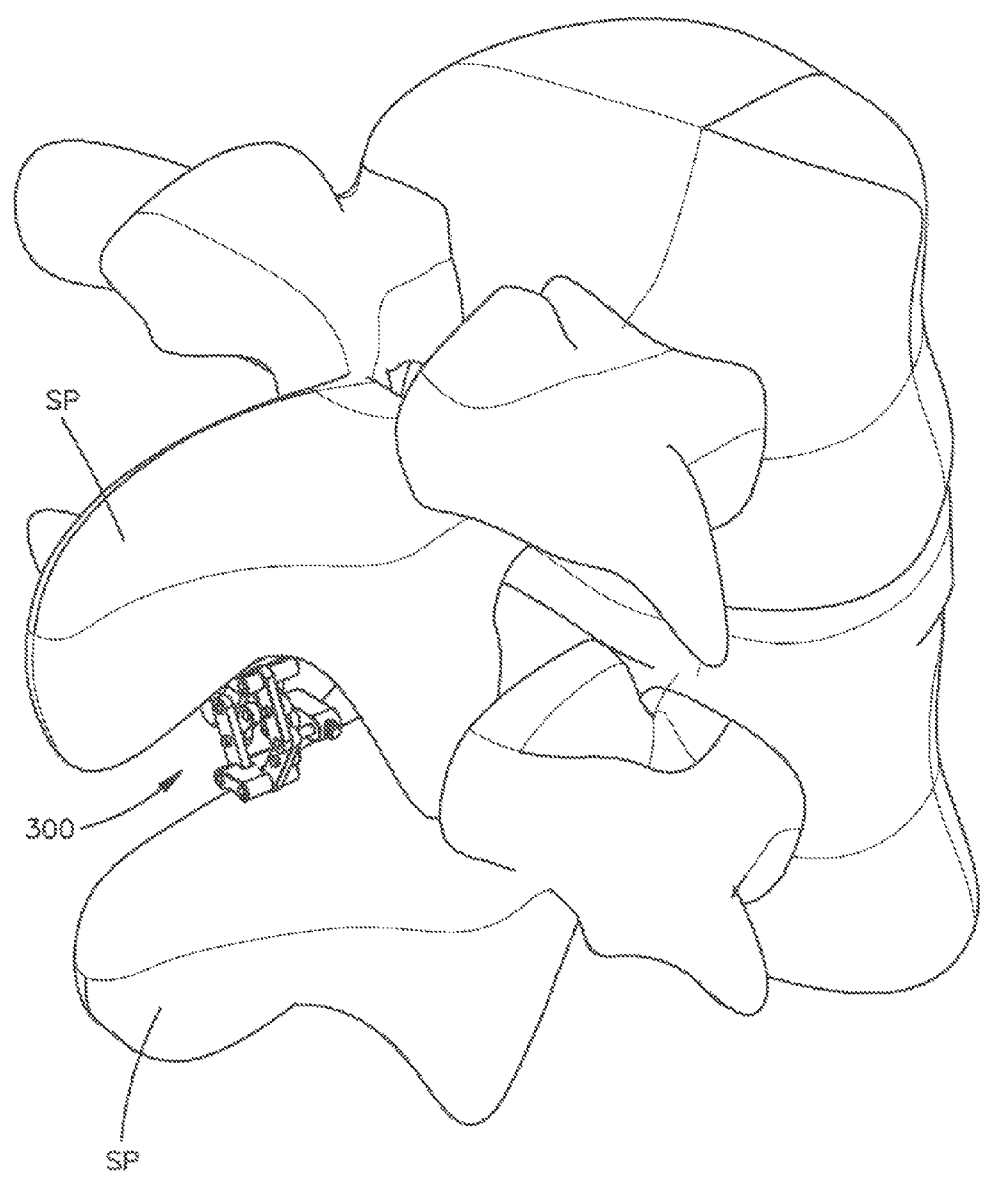

EXPANDABLE INTERSPINOUS PROCESS SPACER

CROSS-REFERENCE TO RELATED APPLICATIONS

This application is a division of U.S. patent application Ser. No. 12/645,289, filed Dec. 22, 2009, now U.S. Pat. No. 8,216, 278, entitled "EXPANDABLE INTERSPINOUS PROCESS SPACER," which claims the benefit of U.S. Provisional Application No. 61/139,794, filed on Dec. 22, 2008, entitled "EXPANDABLE INTERSPINOUS PROCESS SPACER," the contents of which are incorporated in their entireties by reference herein.

BACKGROUND OF THE INVENTION

A human vertebra has a rearwardly projecting portion known as a spinous process. Bending of the spine can cause the spinous processes of adjacent vertebrae to move toward each other. This may, in some people, constrict the space in the spinal canal and foramina and, thus, may cause pain. Such constriction, which is known as stenosis, can be treated by the implantation of an interspinous spacer into the space between adjacent spinous processes.

Current interspinous spacers are typically constructed of separate pieces which require insertion from opposite sides of the spine, in a posterior approach, and necessitate rather large incisions, cutting both left and right thoracolumbar fascia as well as stripping the multifidus muscles from their attachments.

It is desirable to provide an interspinous spacer for implantation between spinous processes of adjacent vertebrae which can be laterally inserted in a first configuration through a single opening in a minimally invasive approach and which may then be deployed to a second configuration to maintain the spacer in position between the adjacent spinous processes.

SUMMARY OF THE INVENTION

The present invention relates generally to an interspinous spacer. More specifically, the present invention is directed to an expandable interspinous process spacer implant for implantation between adjacent spinous processes to treat spinal stenosis. The interspinous process spacer implant is preferably adjustable so that the user can conform the interspinous spacer assembly to the individual anatomy of a patient's spine.

One preferred embodiment of the present invention is an expandable interspinous spacer implant for insertion into an interspinous space between a spinous process of a superior vertebral body and a spinous process of an inferior vertebral body. The implant may include a first pair of proximal legs that are joined in a scissor-like fashion and a second pair of distal legs that are joined in a scissor-like fashion. The distal legs and proximal legs may be pivotally coupled to each other by one or more pins that span the width of the implant, with each leg having multiple slots along its longitudinal axis. One end of each proximal leg may be coupled to the corresponding end of each distal leg by a superior cross pin and the other end of each proximal leg may be coupled to the corresponding second end of each distal leg by inferior cross pins. The implant may also include a first plate coupled to a first pair of roller pins that are disposed between a pair of slots on the legs and a second plate coupled to a second pair of roller pins that are disposed between a pair of slots on the legs, the first plate and second plate each having a hole for receiving a fastener. The fastener being coupled between the first and second plates via the first plate hole and second plate hole. The implant may further include a superior bearing surface coupled between the superior cross pins and an inferior bearing surface coupled between the inferior cross pins, where, rotation of the fastener results in the first plate and the second plate being drawn toward each other causing the expansion of the height of the implant.

In an alternate preferred embodiment, an expandable interspinous process spacer implant may include a first and second pair of proximal legs on its proximal side and a first pair and second pair of distal legs on the distal side. The implant may further include a first plate coupled to the first pair of proximal legs and the first pair of distal legs and a second plate coupled to the second pair of proximal legs and the second pair of distal legs and a fastener coupled between the first and second plates. The implant may further include a superior bearing surface having a first end and a second end where the superior bearing surface joins one of the first pair of proximal legs and one of the second pair of proximal legs at its first end and one of the second pair of proximal legs and one of the second pair of proximal legs at its second end; and an inferior bearing surface having a first end and a second end where the inferior bearing surface joins one of the first pair of proximal legs and one of the second pair of proximal legs at its first end and one of the second pair of proximal legs and one of the second pair of proximal legs at its second end. In this alternate preferred embodiment, rotation of the fastener decreases the distance between the first plate and the second plate and causes an increase of the vertical distance between the superior bearing surface and the inferior bearing surface.

In another alternative embodiment, an expandable interspinous process spacer implant may include a first pair of legs pivotally joined with each other and a second pair of legs pivotally joined with each other. The implant may further include a first plate configured to receive a head portion of a fastener and coupled to the first ends of the first pair of legs and a second plate configured to receive a shaft portion of the fastener and coupled to the first ends of the second pair of legs. The implant may further include a superior bearing surface connecting one of the first pair of legs one of the second pair of legs and an inferior bearing surface connecting the other one of the first pair of legs and the one of the second pair of legs. In this alternate preferred embodiment decreasing the distance between the first plate and the second plate causes an increase in vertical distance between the two bearing surfaces.

BRIEF DESCRIPTION OF SEVERAL VIEWS OF THE DRAWINGS

The foregoing summary, as well as the following detailed description of preferred embodiments of the application, will be better understood when read in conjunction with the appended drawings. For the purposes of illustrating the device of the present application, there is shown in the drawings preferred embodiments. It should be understood, however, that the application is not limited to the precise arrangement, structures, features, embodiments, aspects, and instrumentalities shown, and the arrangements, structures, features, embodiments, aspects and instrumentalities shown may be used singularly or in combination with other arrangements, structures, features, embodiments, aspects and instrumentalities. In the drawings:

FIG. 16 illustrates a side perspective view of the expandable interspinous process spacer shown in FIG. 12 in a collapsed state; and FIG. 17 illustrates a front elevational view of the expandable interspinous process spacer shown in FIG. 12 inserted into an interspinous space between adjacent spinous processes.

DETAILED DESCRIPTION OF CERTAIN EMBODIMENTS

Figure 1:
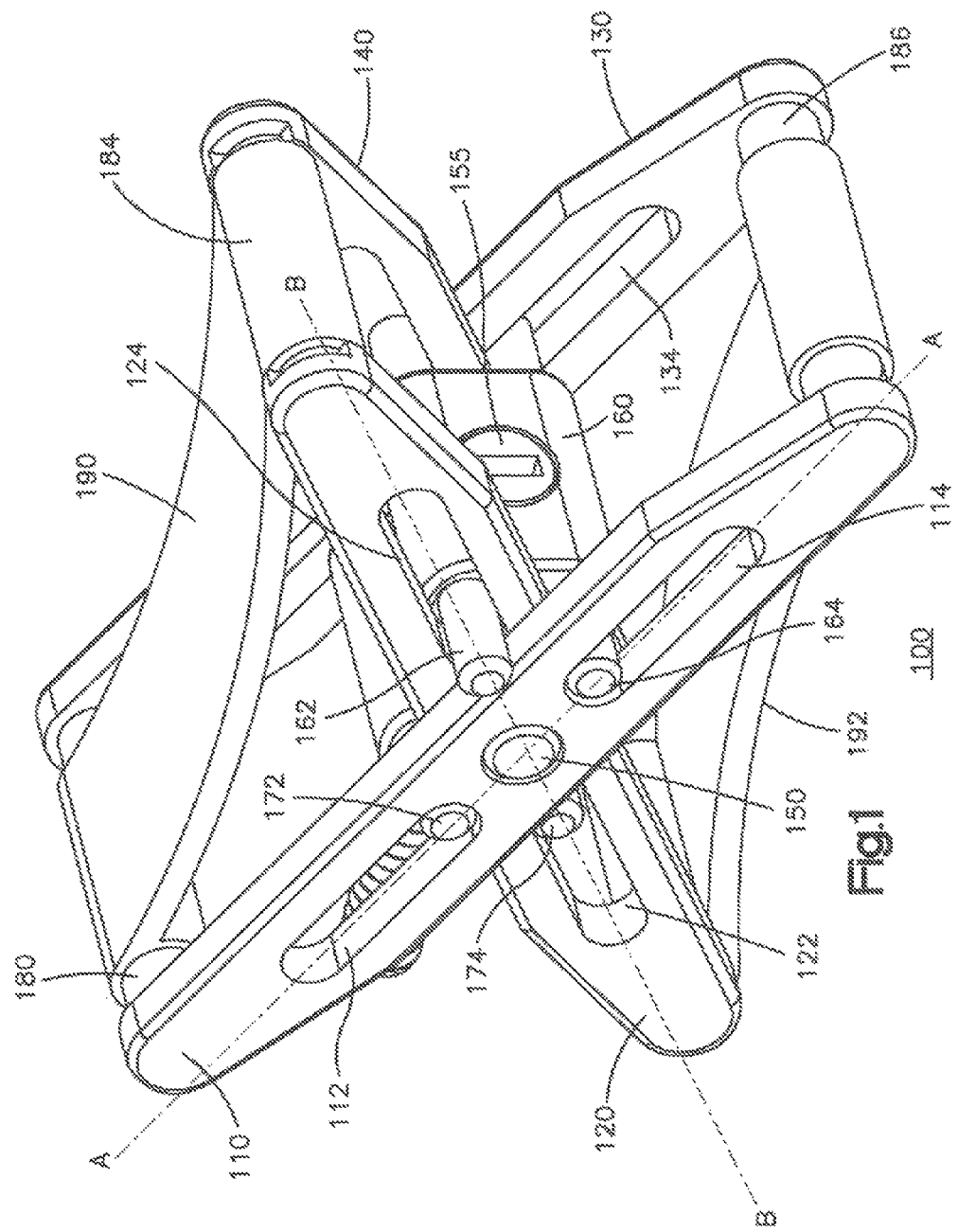
FIG. 1 illustrates a front perspective view of an expandable interspinous process spacer according to a first preferred embodiment of the present invention in an expanded state.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the interspinous spacer and designated parts thereof. The words, "anterior", "posterior", "superior", "inferior", "lateral", "sagittal", "axial", "coronal" and related words and/or phrases designate preferred positions and orientations in the human body to which reference is made and are not meant to be limiting. The terminology includes the above-listed words, derivatives thereof and words of similar import.

Certain exemplary embodiments of the invention will now be discussed with reference to the aforementioned figures wherein like reference numerals refer to like components. In general, such embodiments relate to an expandable interspinous process spacer implant for implantation and/or affixation between spinous processes SP of adjacent vertebrae, including a superior vertebra Vs and an inferior vertebra Vi to treat spinal stenosis or any condition wherein spacing between the spinous processes SP of the adjacent vertebrae Vs, Vi is desired. Although, the implant may have other uses including, for example, as an expandable interbody spacer for use between adjacent vertebral bodies etc.

As will be described in greater detail below, the interspinous spacer implant preferably includes expandable members sized and configured for insertion into the space between adjacent spinous processes SP where it can operatively contact one or more of the adjacent spinous processes SP. The interspinous spacer implant is preferably adjustable so that the user can configure the interspinous spacer implant to fit the anatomy of the patient's spine. The interspinous spacer implant may be fully or partially adjustable. For example, the height, width and/or angle of the spacer implant may be adjustable. Alternatively, only the height, or the width of the spacer may be adjustable, or the spacer may be non-adjustable. Moreover, the height, width and/or the angle of the spacer member may be adjustable to only a certain extent or limit. Likewise, the method of implanting the interspinous spacer preferably allows a surgeon to adjust the interspinous spacer and/or the orientation of the interspinous spacer in the patient.

Referring to FIGS. 1-5, a first preferred embodiment of an expandable interspinous process spacer implant 100 which is sized and configured for insertion into an interspinous space between adjacent spinous processes SP and coupling thereto, includes on its proximal side a first leg 110 and a second leg 120 that are joined in scissor-like fashion by a fulcrum pin 150 that extends through the width of the implant 100 to couple a third leg 130 and a fourth leg 140 in scissor-like fashion on the distal side of the implant 100. The fulcrum pin 150 may extend through the width of the implant 100 to couple the two pairs of legs 110, 120, 130, 140, or alternatively may be replaced by two separate pins or other coupling mechanism (not shown) that serves the same function of coupling in scissor-like fashion the first and second legs 110, 120 and the third and fourth legs 130, 140. Additionally, a first cross pin 180 preferably connects the first end of the first leg 110 to the first end of the third leg 130 and a second cross pin 182 connects the first end of the second leg 120 to the first end of the fourth leg 140. Similarly, a third cross pin 184 connects the second end of the second leg 120 to the second end of the fourth leg 140 and a fourth cross pin 186 connects the second end of the first leg 110 to the second end of the third leg 130.

In the first preferred embodiment, the first leg 110 has a first slot 112 and a second slot 114 formed through it along its longitudinal axis A-A and the second leg 120 has a third slot 122 and a fourth slot 124 along its longitudinal axis B-B. Similarly, third leg 130 has a fifth slot 132 and a sixth slot 134 along its longitudinal axis C-C and fourth leg 140 has a seventh slot 142 and an eighth slot 144 along its longitudinal axis D-D.

In order to couple the second leg 120 to the fourth leg 140, a first roller pin 162 is preferably coupled to and spans between the fourth slot 124 and the eighth slot 144 and a second roller pin 174 is coupled to and spans between the third slot 122 and the seventh slot 142. Similarly, in order to couple the first leg 110 and the third leg 130 a third roller pin 164 is preferably coupled to and spans between the second slot 114 and the sixth slot 134 and a fourth roller pin 172 is coupled to and spans between the first slot 112 and the fifth slot 132. In certain embodiments, the first, second, third and fourth roller pins 162, 174, 164 and 172, can additionally include a wear resistant coating.

A first plate member 160 is preferably fixed between the first roller pin 162 and the third roller pin 164 and a second plate member 170 is preferably fixed between the second roller pin 174 and the fourth roller pin 172. Alternatively, the first plate 160 and the first and second roller pins 162, 164 can be a single element formed from the same piece of material as opposed to multiple elements. Similarly, the second plate 170 and the third and fourth roller pins 172, 174 can be a single element formed from the same piece of material. In the first preferred embodiment, the first plate 160 preferably has a first hole (not shown) to accommodate the head of fastener 155 the second plate 170 has a second hole (not shown) to accommodate the threaded shaft portion of fastener 155. Each of the first hole used to accommodate the head of fastener 155 and the second hole used to accommodate the threaded shaft portion of fastener may be threaded or unthreaded. In one preferred embodiment fastener 155 is an expansion screw that includes threading or other similar mechanism the tightening of which permits movement of the spacer 100 from a collapsed position to an expanded position. In order to accommodate expansion screw 155, a hole may be disposed through the fulcrum pin 150 or in the alternative, two disconnected fulcrum pins, as discussed above, can accommodate the positioning of the expansion screw 155. Alternatively, implant 100 may be modified so that expansion screw 155 can be inserted just above or just below fulcrum pin 150.

Figure 2:
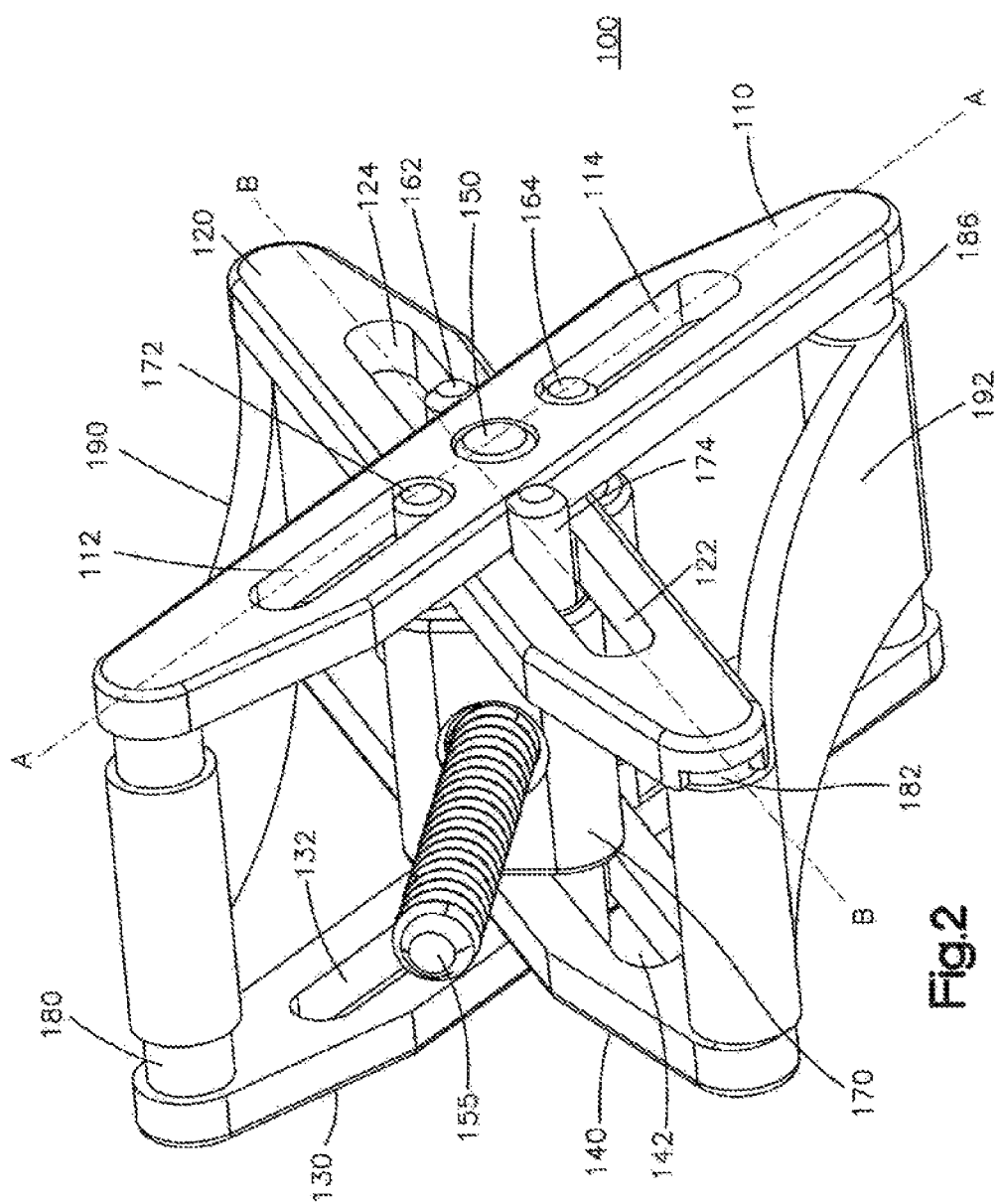
FIG. 2 illustrates a side perspective view of the expandable interspinous process spacer shown in FIG. 1.
Figure 3:
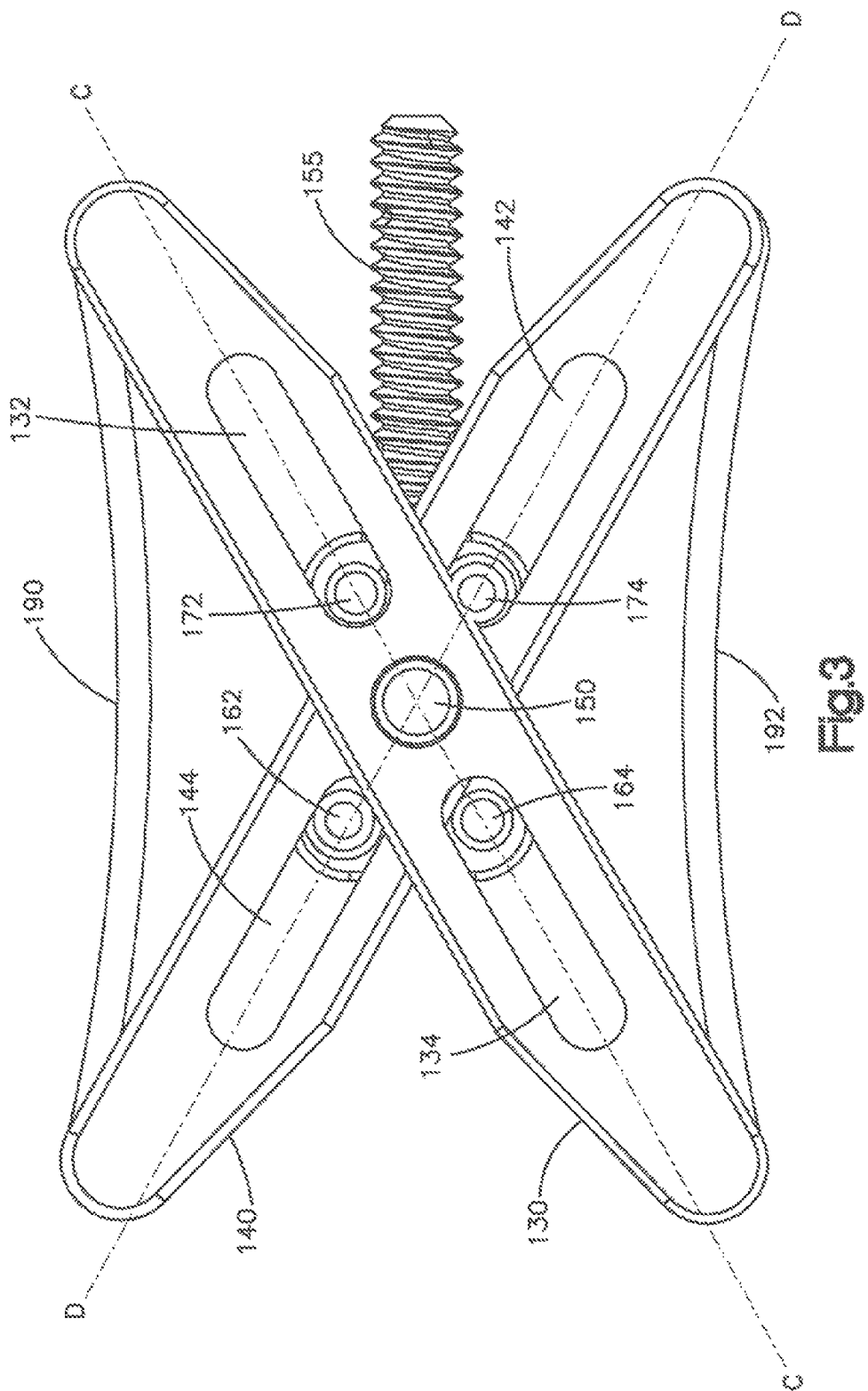
FIG. 3 illustrates a side elevational view of the expandable interspinous process spacer shown in FIG. 1.

In a first preferred embodiment, as can be seen in FIGS. 1-3, a superior bearing surface 190 is disposed between the first cross pin 180 and the third cross pin 184. An inferior bearing surface 192 is similarly disposed between the second cross pin 182 and the fourth cross pin 186. The superior and inferior bearing surfaces 190, 192 are configured to bear against an inferior surface of a superior spinous process SP and the superior surface of the inferior spinous process SP, respectively. In a preferred embodiment, the bearing surfaces 190, 192 are constructed of segmented polyether urethane, which may be marketed under the tradename BioSpan®. However, the bearing surfaces 190, 192 are not limited to polyether urethane constructions and may be constructed of nearly any material that is able to take on the general shape of the bearing surfaces 190, 192 and withstand their normal operating conditions, such as a demineralized allograft sheet. A range of material compositions can be chosen for the superior and inferior bearing surfaces 190, 192, the choice of which can be tailored to provide a desired flexibility or other characteristic of the implant 100. For example, if a polycarbonateurethane (peU) material is chosen to form the superior and inferior bearing surfaces 190, 192, the implant 100 may exhibit high flexibility, whereas if a polyethylene mesh is chosen to form the superior and inferior bearing surfaces 190, 192, the implant 100 typically exhibits less flexibility. As can be seen in FIGS. 1-3, in the present embodiment, only first cross pin 180 and fourth cross pin 186 is visible outside of the bearing surfaces however, as can be appreciated by one of ordinary skill in the art, any combination of cross pins may be visible or not visible depending on the dimensions of such cross pins and the dimensions of the bearing surfaces.

The superior and inferior bearing surfaces 190, 192 can further include a treatment to allow for or deter bony ingrowth to accommodate either a fusion or non-fusion application. The above-listed elements of the implant 100 may be formed from a range of biocompatible materials, including titanium, stainless steel, cobalt-chrome, ultra-high molecular weight polyethylene (UHMWPE), or polymers such as polyetheretherketone (PEEK).

Figure 4:
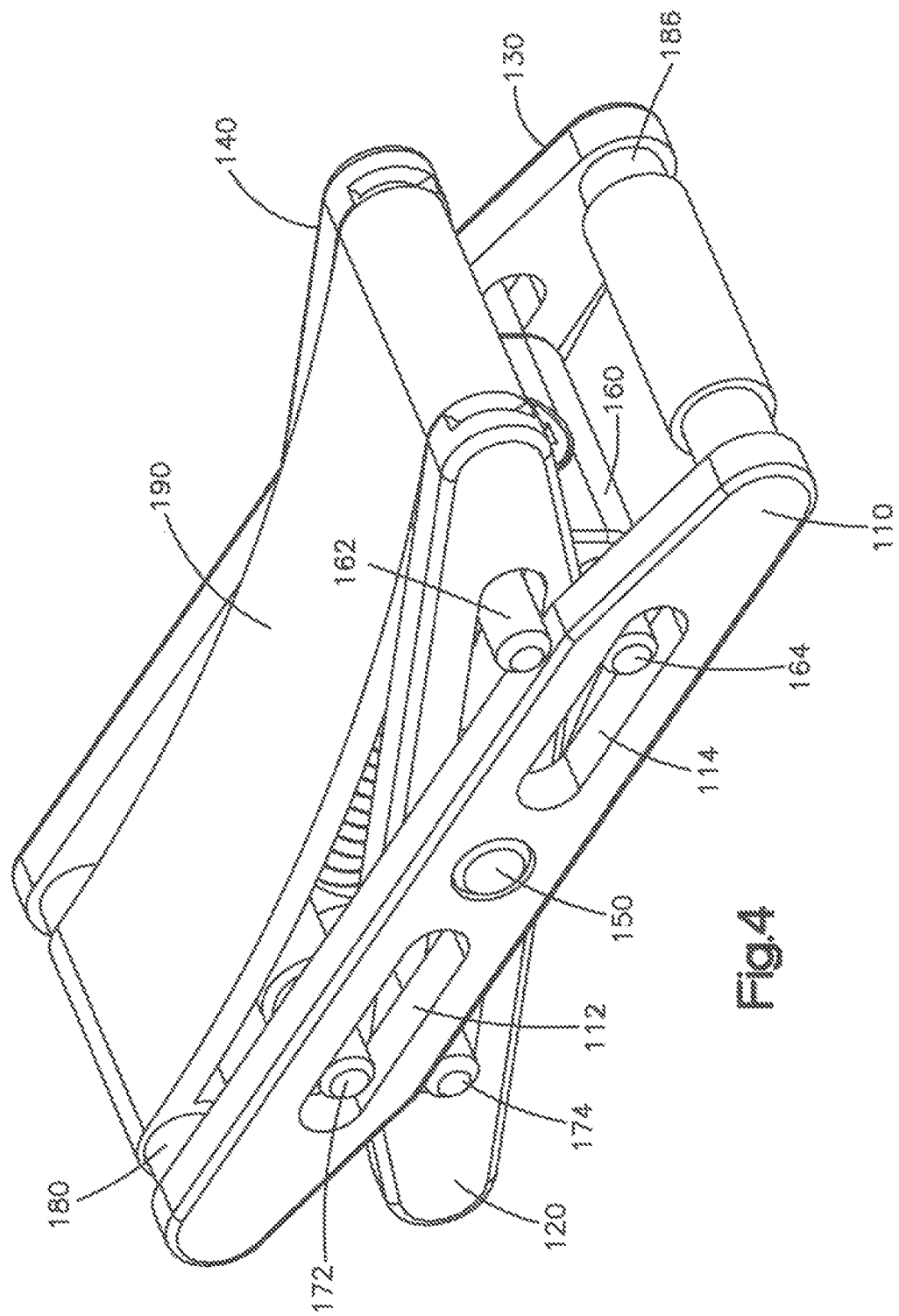
FIG. 4 illustrates a front perspective view of the expandable interspinous process spacer shown in FIG. 1 in a collapsed state.
Figure 5:
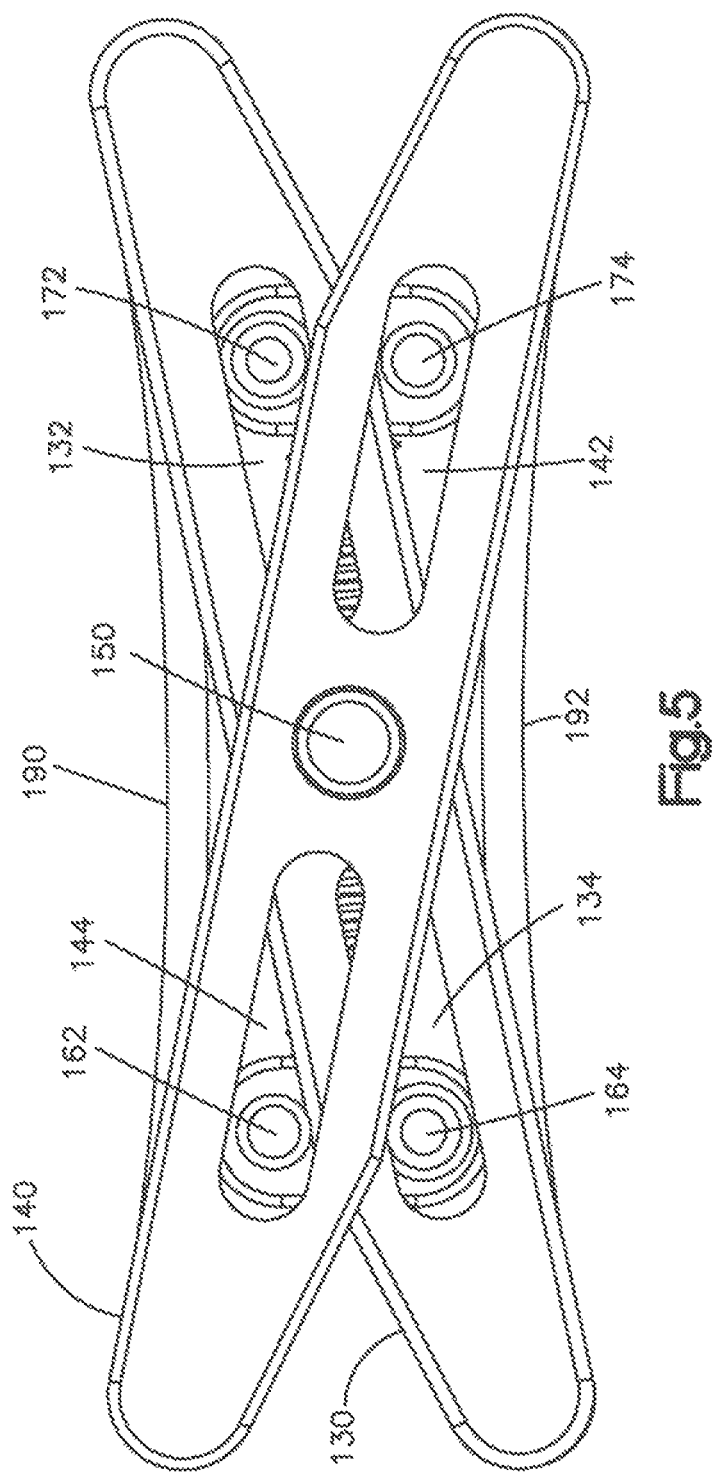
FIG. 5 illustrates a side elevational view of the expandable interspinous process spacer shown in FIG. 1 in a collapsed state.
Figure 6:
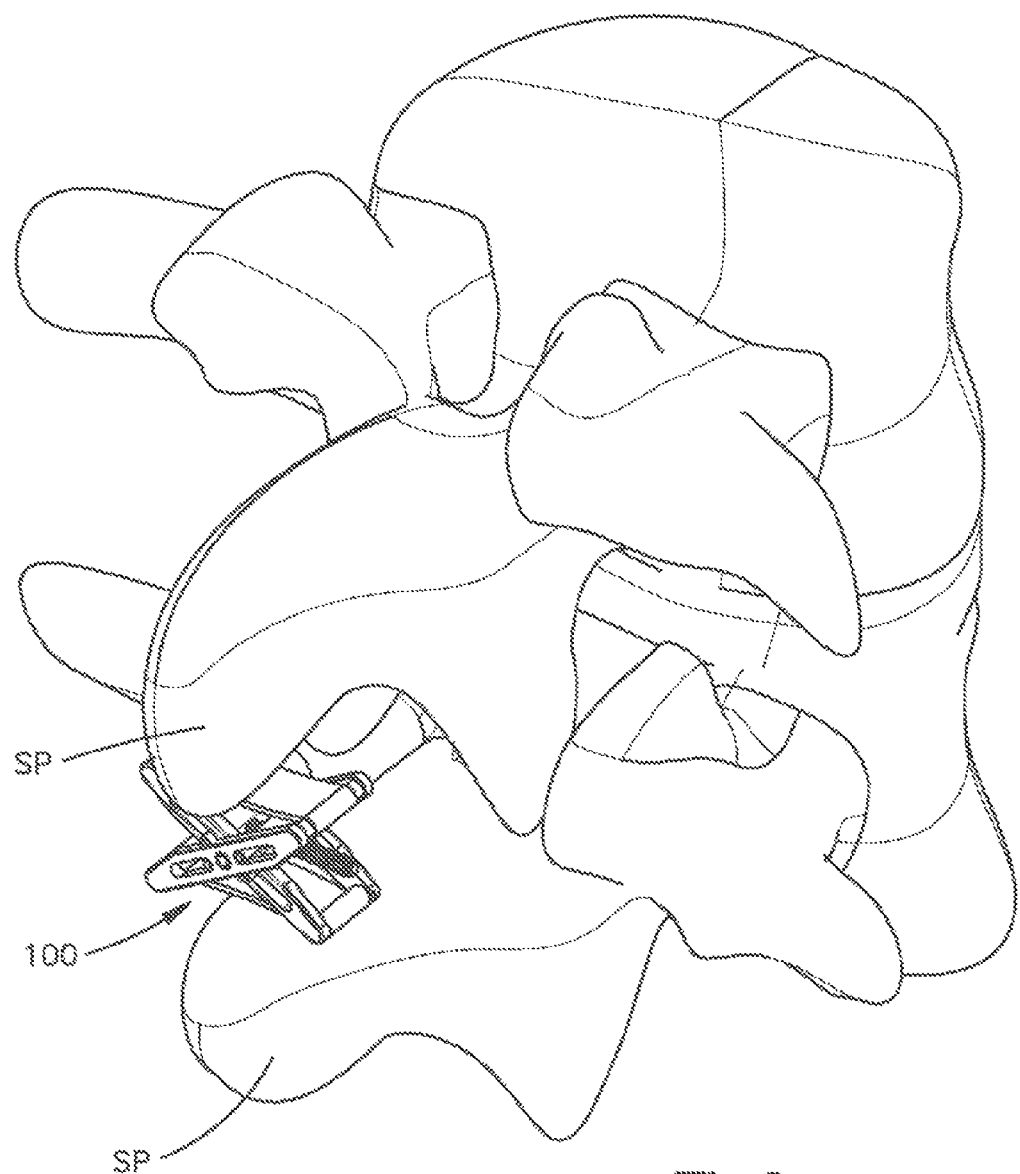
FIG. 6 illustrates a perspective view of the expandable interspinous process spacer shown in FIG. 1 inserted into an interspinous space between adjacent spinous processes.

The interspinous process spacer 100 of the first preferred embodiment is adjustable from a non-expanded, collapsed configuration as shown in FIG. 4 to an expanded deployed configuration as shown in FIGS. 1-3. Spacer 100 may be adapted to the patient's anatomy during implantation by adjusting the height of spacer 100. Moreover, as will be appreciated by one of ordinary skill in the art, the angulation of the spacer 100 may be adjusted by independently adjusting the anterior and posterior ends of spacer 100. FIG. 6 illustrates a preferred use of the spacer 100 implanted in the spine, between spinous processes SP of adjacent vertebrae.

One exemplary surgical technique for implanting spacer 100 is described below, however, those skilled in the art will appreciate that spacer 100 may be implanted utilizing numerous techniques and/or surgical steps that would be apparent to one having ordinary skill in the art, following a review of the disclosure herein.

In use, the interspinous process spacer 100 is implanted to treat patients with spinal stenosis. A lateral or medial lateral approach corridor is provided and the interspinous ligament is preferably pierced or partially removed although the interspinous ligament may be left intact. The implant 100 is preferably inserted laterally through the approach corridor in a collapsed configuration and is implanted between the adjacent spinous processes. Once the implant 100 is positioned, an instrument is introduced through the corridor and coupled to an instrument engagement feature on the head of the expansion screw 155. The expansion screw 155 is actuated, preferably through rotation, causing the threaded shaft of the expansion screw 155 to interact with the screw hole of the second plate 170 and thereby drawing the first plate 160 and the second plate 170 toward the center of the implant 100.

As the first plate 160 and the second plate 170 are drawn toward the center of the implant 100, the ends of the first, second, third and fourth roller pins 162, 174, 164 and 174 actuate within their respective slots to enlarge implant 100 into a more expanded state. Additionally, the drawing together of the first and second plates 160, 170, and the resultant movement of the roller pins forces the superior bearing surface 190 and the inferior bearing surface 192 to be distracted from one another and the height of the implant 100, at least at the ends of the first, second, third and fourth legs 110, 120, 130, 140 to increase.

Once the screw 155 had been tightened, the implant 100 is prevented from collapsing due to interference created between the threading on the screw 155, and the screw hole on the second plate 170 which is preferably threaded. Alternately or in addition thereto, the screw 155 may be locked after the expansion of the implant, e.g., by placing a nut on the distal end of the screw opposite the second plate 170. Once the desired spacing between the adjacent spinous processes has been achieved, the instrument is removed and the wound is closed. The implant 100 is not limited to lateral or minimally invasive insertions and may be implanted from a posterior approach or a posterior-lateral approach and/or through a mini-open or open incision in a patient.

In certain embodiments of the present invention, implant 100 may also include an engagement mechanism for engaging one or more of the spinous processes SP. The engagement mechanism may include wings, plates, hooks, etc. that prevent migration of the interspinous spacer implant. In certain embodiments the engagement mechanism may be adjustable in length, bendable, polyaxial with respect to the spacer to enable adaptability to the individual anatomy of a particular patient's spine and prevent migration of the interspinous spacer implant once implanted into the patient. In use, the engagement member may engage the patient's spinous processes SP in a variety of different ways including, for example, via one or more screws, bolts, rivets, spikes, or other protrusions and/or via compression. As would be appreciated by one with ordinary skill in the art, the engagement mechanism may be operatively coupled to the interspinous spacer member or members in a variety of different ways.

The implant 100 can also be modified to form an expandable interbody spacer. In such a configuration, the superior and inferior bearing surfaces 190, 192 can be formed from a number of materials, such as nitinol, titanium, stainless steel, mineralized or demineralized allograft, or polymers such as PEEK or segmental polyether urethane that can be flexible or inflexible and may be capable of supporting or assisting in supporting the necessary loads. In one embodiment, if inflexible materials are used for either or both of bearing surfaces 190 and 192, any or all of the holes that engage the cross pins 180, 182, 184 and 186 may be elongated in order to facilitate motion. Alternatively, the implant 100 can be designed such that the loads are borne by the ends of the first, second, third, and fourth arms 110, 120, 130, 140, and/or the first, second, third, and fourth crosspins 180, 182, 184, 186. In such an arrangement, the ends of the first, second, third, and fourth arms 110, 120, 130, 140, and/or the first, second, third, and fourth crosspins 180, 182, 184, 186 may further include surface features, such as spikes, ridges, or teeth (not shown) to help the securing of the implant 100 to the desired anatomical structures, e.g., vertebral body endplates.

In this configuration, the implant 100 may include one or more axial bores (not shown) through the implant 100 along its height to accommodate graft material or boney growth therethrough. Alternatively, the implant 100 can be modified to form an expandable total disc replacement device, in which the superior and inferior bearing surfaces 190, 192 include convex geometries to allow for motion between the superior and inferior vertebrae, respectively. Additionally, the implant 100 can be modified slightly to form a cavity creation device for the interior of an osteoporotic vertebral body or a vertebral body suffering from a compression fracture. In addition to a cavity creation device, the modified implant 100 of such a configuration can further be left on the interior of the osteoporotic vertebral body as a height maintaining stand alone device or in conjunction with bone cement or other void filler as is known in the art.

Referring to FIGS. 7-11, a second preferred embodiment of the expandable interspinous process spacer implant 200 which is sized and configured for insertion into an interspinous space between adjacent spinous processes SP, will now be described. Implant 200 includes on its proximal side a first leg 210, and a second leg 220 towards one end of the implant and a third leg 230 and fourth leg 240 towards the other end of the implant. Similarly on its distal side, implant 200 includes a fifth leg 250 and a sixth leg 260 towards one end of the implant and a seventh leg 270 and eighth leg 280 towards the other end of the implant.

Additionally, implant 200 includes on its proximal side extension members 242 and 244 that are coupled to each other and in contact with third leg 230 and fourth leg 240. In one embodiment, third leg 230 may have an indentation that accepts side extension 242 when the implant is collapsed. Similarly, implant 200 includes on its distal side proximal side extension members 262 and 264 that are coupled to each other and in contact with sixth leg 260 and seventh leg 270. In one embodiment, seventh leg 270 may have an indentation that accepts side extension 262 when the implant is collapsed.

A first plate member 225 is preferably coupled to the lower portions of first leg 210 and fifth leg 250 and the upper portions of second leg 220 and sixth leg 260 via a pin or other connector as is known in the art. Similarly, a second plate member 235 is coupled to the lower portions of third leg 230 and seventh leg 270 and the upper portions of fourth leg 240 and eighth leg 280. First plate 225 preferably has a first hole (not shown) to accommodate the head of fastener 245 and the second plate 235 has a second hole 255 to accommodate the threaded shaft portion of fastener 245. Fastener 245 is preferably an expansion screw that includes threading or other similar mechanism the tightening of which permits movement of the spacer 200 from a collapsed position to an expanded position.

A first cross pin 215 preferably connects the top end of the first leg 210 to the top end of the fifth leg 250 and a second cross pin 285 connects the top end of the third leg 230 to the top end of the seventh leg 270. Similarly, a third cross pin 295 connects the bottom end of the second leg 220 to the bottom end of the sixth leg 260 and a fourth cross pin 296 connects the bottom end of the fourth leg 240 to the bottom end of the eighth leg 280.

A superior bearing surface 290 is disposed between the first cross pin 215 and the second cross pin 285. An inferior bearing surface 292 is similarly disposed between the third cross pin 295 and the fourth cross pin 296. The superior and inferior bearing surfaces 290 and 292 are configured to bear against an inferior surface of a superior spinous process SP and the superior surface of the inferior spinous process SP, respectively. As can be seen in FIGS. 7-10, in the present embodiment, only second cross pin 285 is visible outside of the bearing surfaces however, as can be appreciated by one of ordinary skill in the art, each of the cross pins may be visible depending on the dimensions of such cross pins and the dimensions of the bearing surfaces. In a preferred embodiment, the bearing surfaces 290 and 292 are constructed of an inflexible material such as Ti and its alloys or PEEK etc. However, the bearing surfaces 290 and 292 may be constructed of nearly any material that is able to take on the general shape of the bearing surfaces 290 and 292 and withstand their normal operating conditions.

Figure 7:
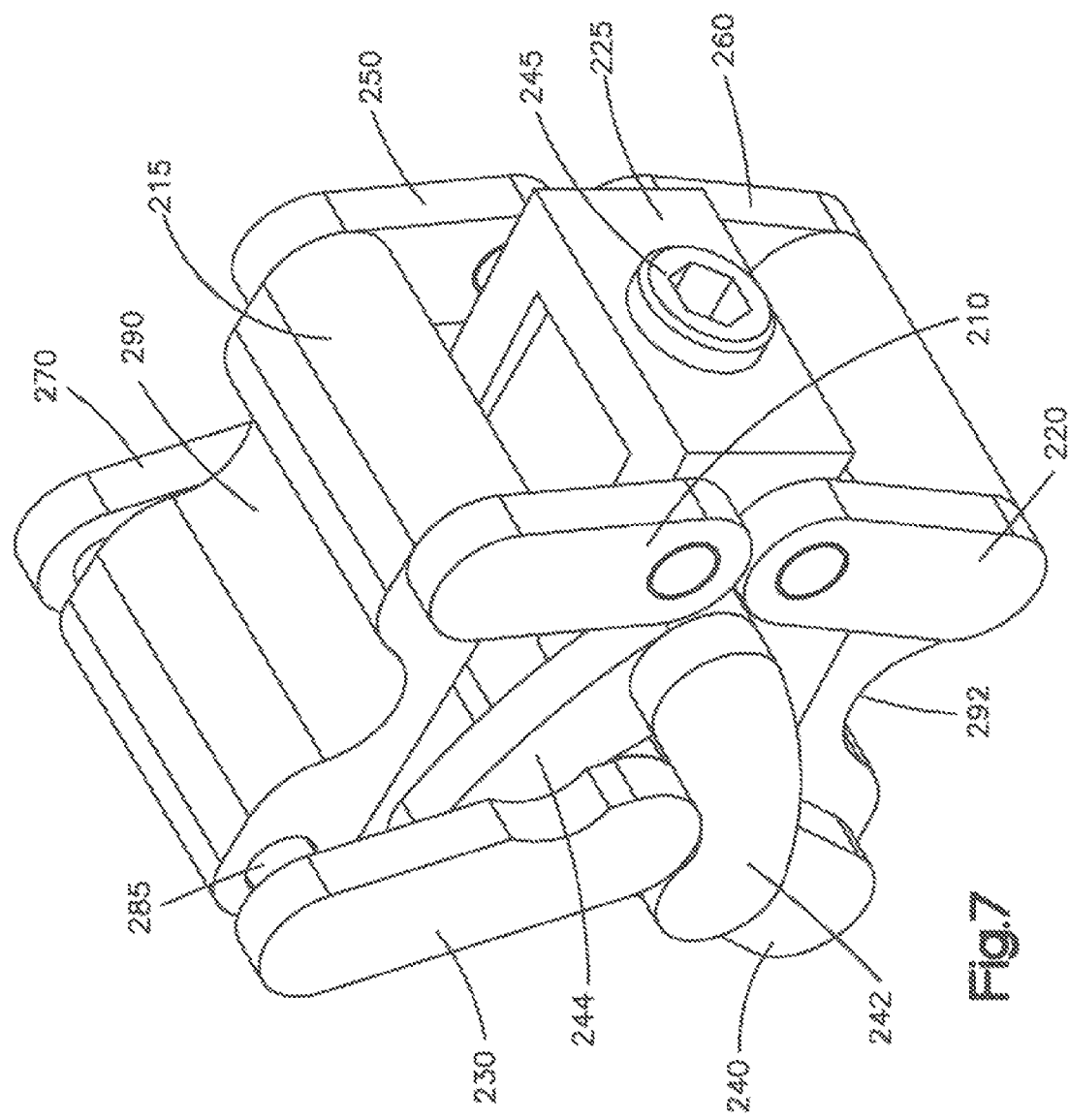
FIG. 7 illustrates a front perspective view of an expandable interspinous process spacer according to a second preferred embodiment of the present invention in an expanded state.
Figure 8:
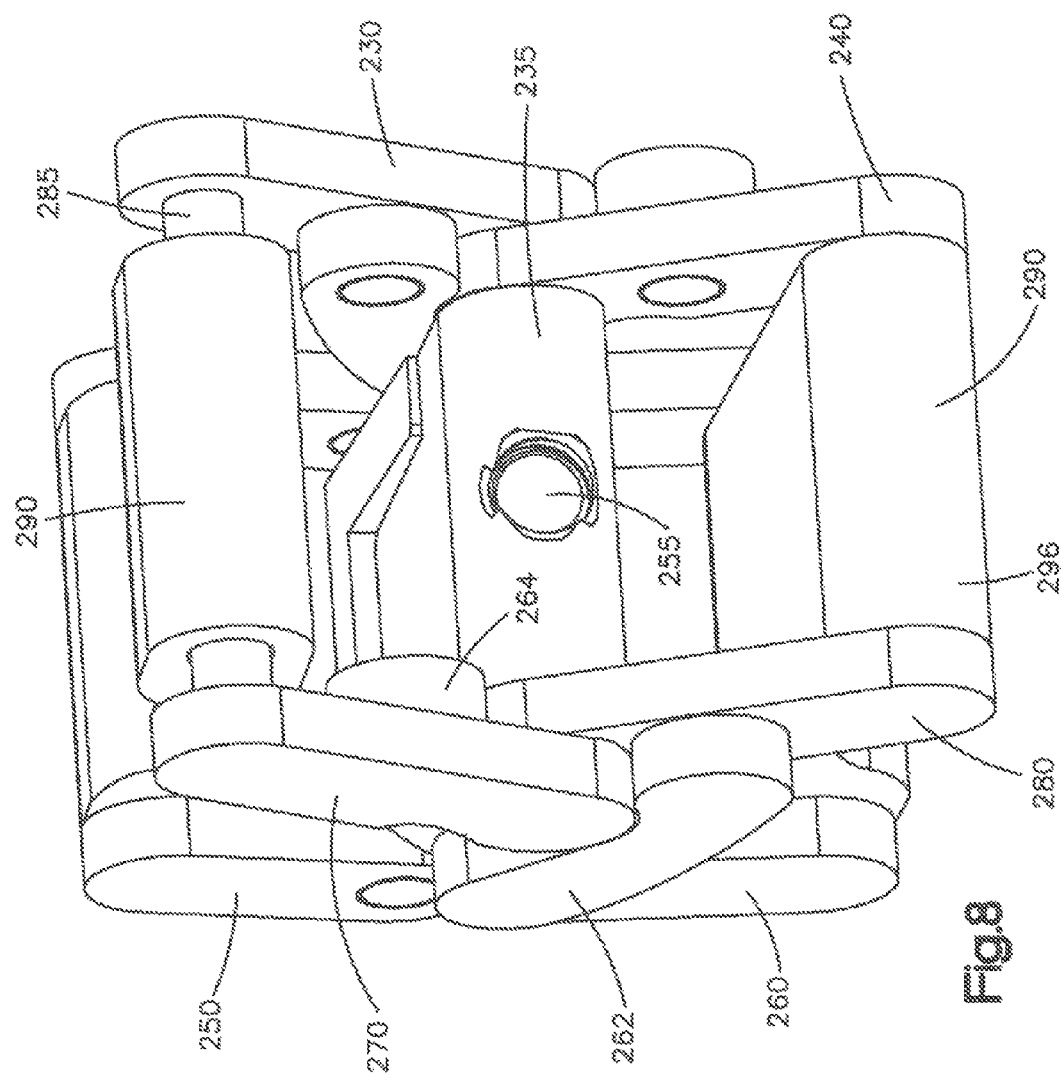
FIG. 8 illustrates a side perspective view of the expandable interspinous process spacer shown in FIG. 7.
Figure 9:
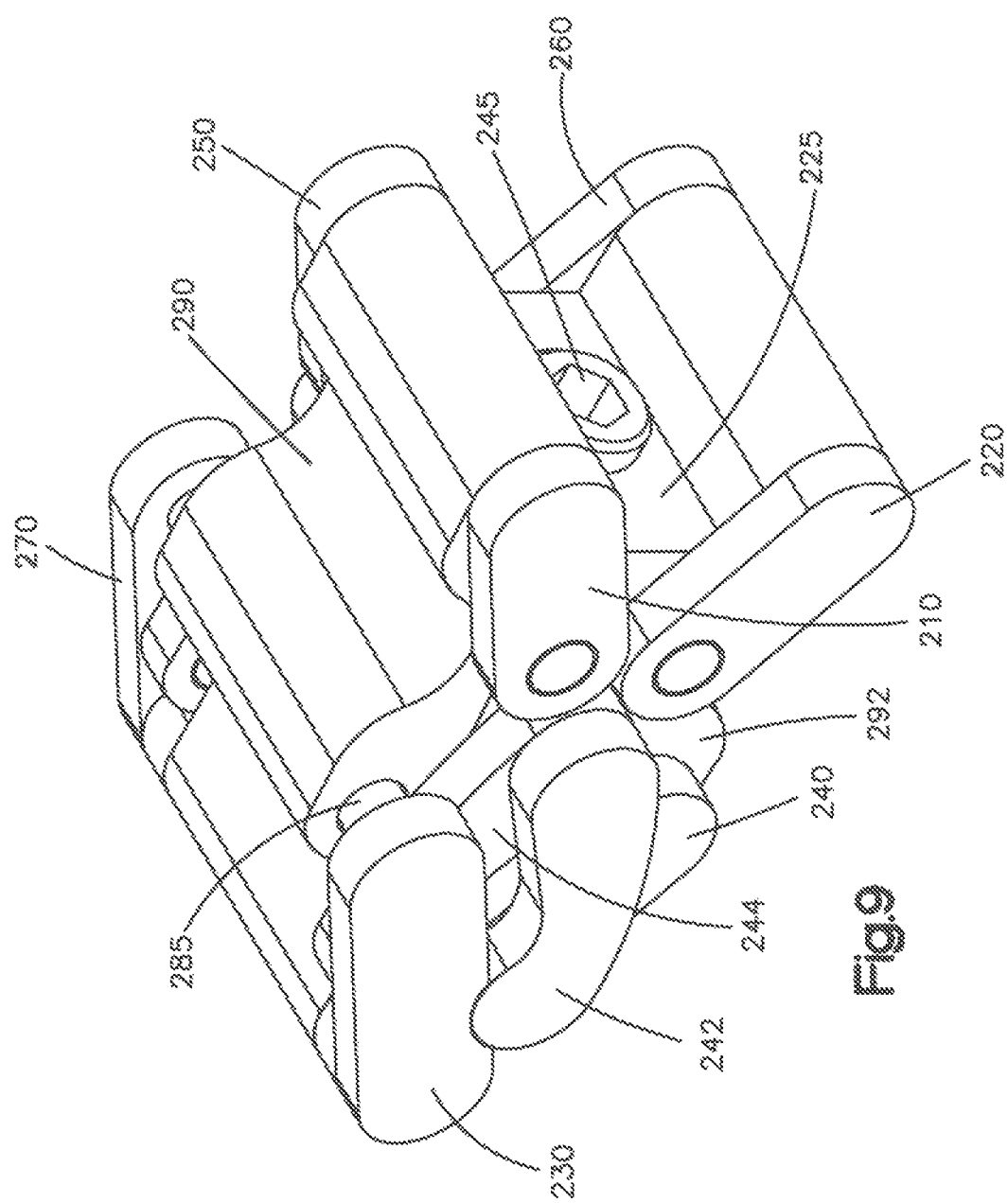
FIG. 9 illustrates a front perspective view of the expandable interspinous process spacer shown in FIG. 7 in a collapsed state.
Figure 10:
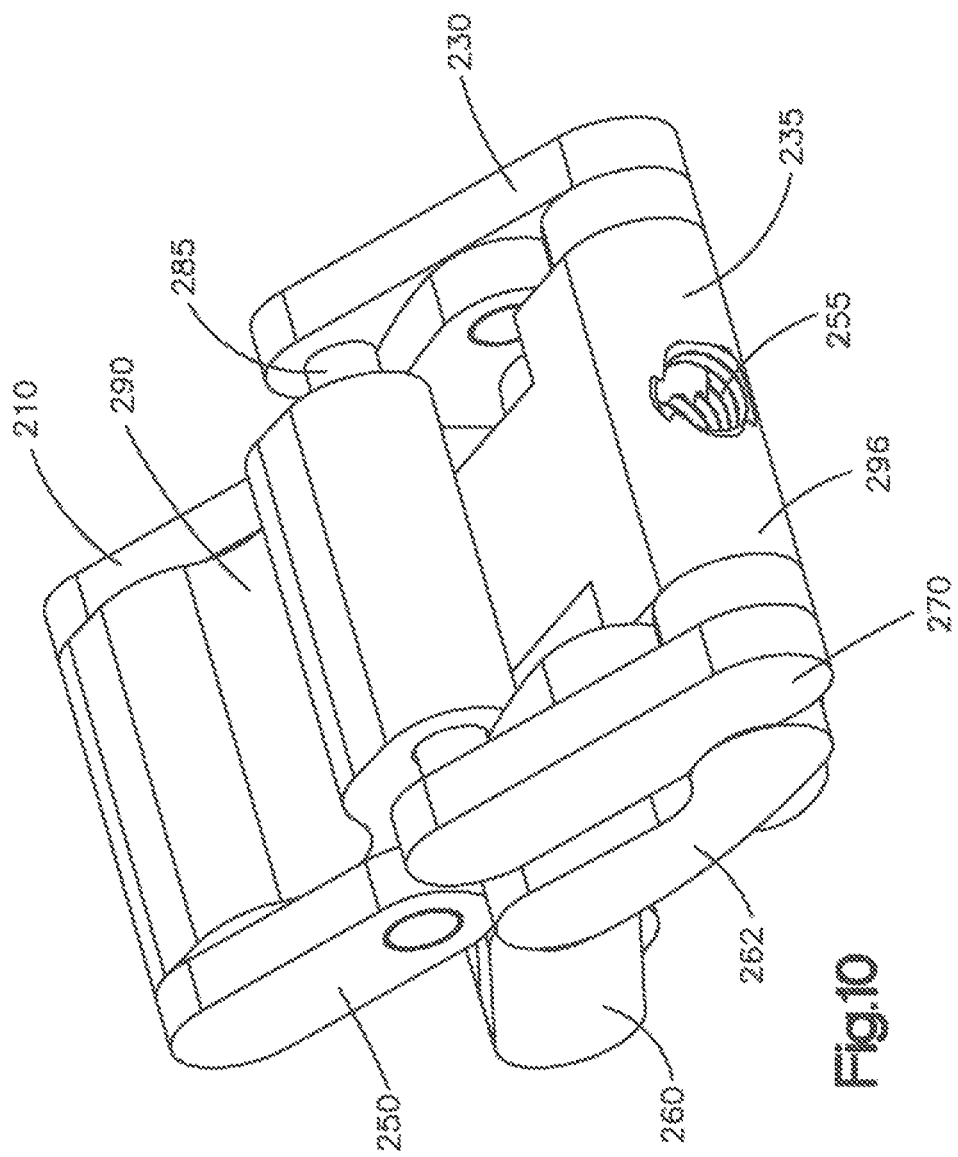
FIG. 10 illustrates a side perspective view of the expandable interspinous process spacer shown in FIG. 7 in a collapsed state.
Figure 11:
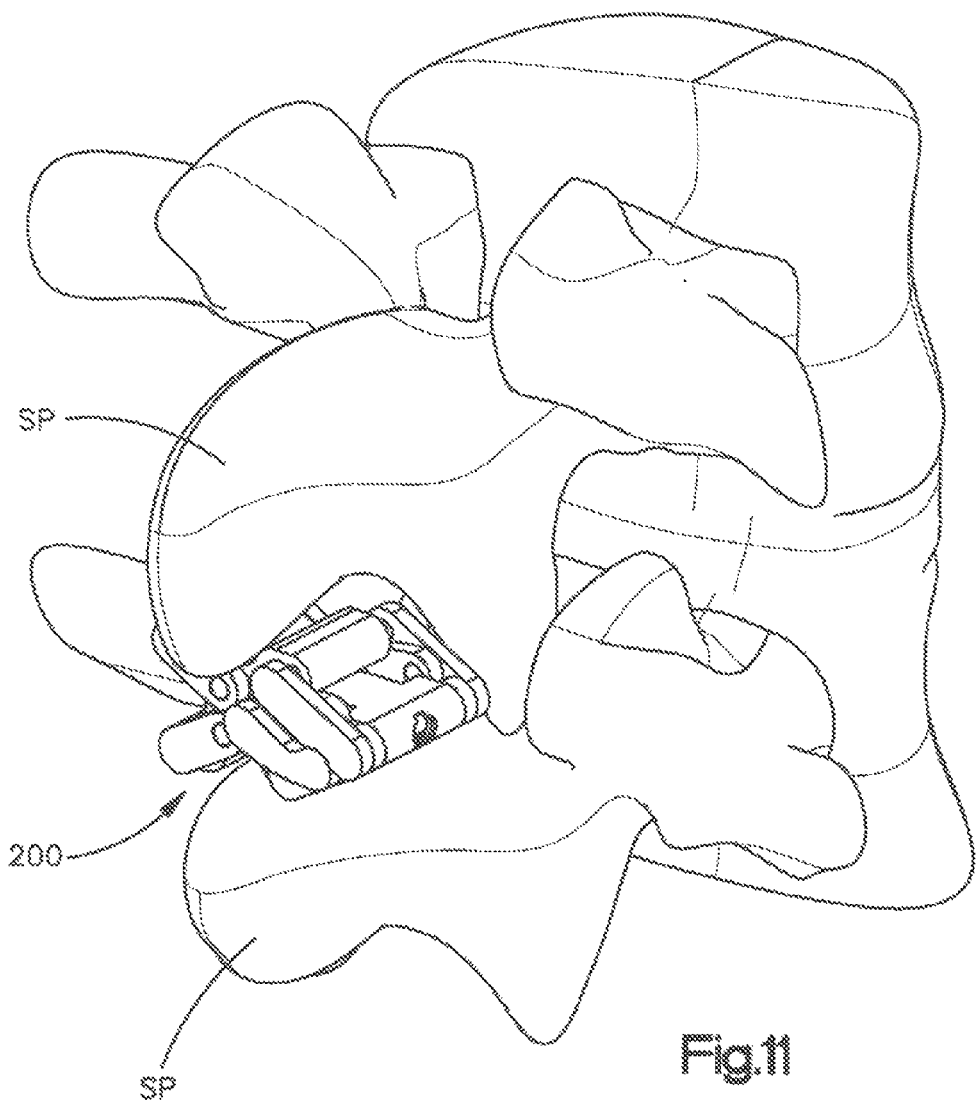
FIG. 11 illustrates a perspective view of the expandable interspinous process spacer shown in FIG. 7 inserted into an interspinous space between adjacent spinous processes.

The interspinous process spacer 200 of the second preferred embodiment is adjustable from a non-expanded, collapsed configuration as shown in FIGS. 9-10 to an expanded deployed configuration as shown in FIGS. 7-8. Spacer 200 may be adapted to the patient's anatomy during implantation by adjusting the height of spacer 200. Moreover, as will be appreciated by one of ordinary skill in the art, the angulation of the spacer 200 may be adjusted by independently adjusting the anterior and posterior ends of spacer 200. FIG. 11 illustrates a preferred use of the spacer 200 implanted in the spine, between spinous processes SP of adjacent vertebrae.

One exemplary surgical technique for implanting spacer 200 is described below, however, those skilled in the art will appreciate that spacer 200 may be implanted utilizing numerous techniques and/or surgical steps that would be apparent to one having ordinary skill in the art, following a review of the disclosure herein.

In use, the interspinous process spacer 200 is implanted to treat patients with spinal stenosis. A lateral or medial lateral approach corridor is provided and the interspinous ligament is preferably pierced or partially removed although the interspinous ligament may be left intact. The implant 200 is preferably inserted laterally through the approach corridor in a collapsed configuration and is implanted between the adjacent spinous processes. Once the implant 200 is positioned, an instrument is introduced through the corridor and coupled to an instrument engagement feature on the head of the expansion screw 245. The expansion screw 245 is actuated, preferably through rotation, causing the threaded shaft of the expansion screw 245 to interact with the screw hole 255 of the second plate 235 and thereby drawing the first plate 225 and the second plate 235 toward each other toward the center of the implant 200.

As the first plate 225 is drawn toward the second plate 235, the top end of the first leg 210 and the top end of the fifth leg 250 as well as the bottom end of the second leg 220 and the bottom end of the sixth leg 260 move away from the center of the implant 200. Similarly, the bottom end of the third leg 230 and the bottom end of the seventh leg 270 as well as the top end of fourth leg 240 and the top end of eighth leg 280 move away from the center of implant 200 to enlarge implant 200 into a more expanded state. This also causes extension member 242 to be drawn away from extension member 244 and interact with the indentation of leg 230 and extension member 262 to be drawn away from extension member 264 and interact with the indentation of leg 270. Moreover, the drawing together of the first and second plates 225 and 235 and the resultant movement of the legs forces the superior bearing surface 290 and the inferior bearing surface 292 to be distracted from one another and the height of the implant 200, at least at the ends of the legs 210, 220, 230, 240, 250, 260, 270 and 280 to increase.

Once the screw 245 had been tightened, the implant 200 is prevented from collapsing due to interference created between the threading on the screw 245, and the screw hole 255 on the second plate 235 which is preferably threaded. Alternately or in addition thereto, the screw 245 may be locked after the expansion of the implant, e.g., by placing a nut on the distal end of the screw opposite the second plate 235. Once the desired spacing between the adjacent spinous processes has been achieved, the instrument is removed and the wound is closed. The implant 200 is not limited to lateral or minimally invasive insertions and may be implanted from a posterior approach or a posterior-lateral approach and/or through a mini-open or open incision in a patient.

Referring to FIGS. 12-17, a third preferred embodiment of the expandable interspinous process spacer implant 300 which is sized and configured for insertion into an interspinous space between adjacent spinous processes SP, will now be described. Implant 300 includes a first leg 310, second leg 320, third leg 330 and fourth leg 340.

In this third preferred embodiment, first leg 310 is pivotally coupled to fourth leg 340 via connectors 311 and 312. More specifically, connector 311 is pivotally coupled via a fulcrum pin 316 to first leg 310 and connector 312 is pivotally coupled via fulcrum pin 317 to fourth leg 340. Similarly, second leg 320 is pivotally coupled to third leg 330 via connectors 321 and 322. More specifically, connector 321 is pivotally coupled via a fulcrum pin 326 to second leg 320 and connector 322 is pivotally coupled via fulcrum pin 327 to third leg 330. Additionally, connectors 311 and 312 are coupled to each other and to expander 315 via cross pin 318 and connectors 321 and 322 are coupled to each other and to expander 315 via cross pin 328. Although the coupling mechanisms described herein may be described as a fulcrum pin or cross pin, it will be appreciated by one with skill in the art that other coupling mechanisms can alternatively or additionally be used.

A first plate member 325 is preferably coupled to the lower portion of first leg 310 and the upper portion of fourth leg 340 via cross pin 335 or other connector as is known in the art. Similarly, a second plate member 345 is coupled to the lower portion of second leg 320 and the upper portion of third leg 330 via cross pin 336. First plate 325 preferably has a first hole (not shown) to accommodate the head of fastener 355 and the second plate 345 has a second hole (not shown) to accommodate the threaded shaft portion of fastener 355. Fastener 355 is preferably an expansion screw that includes threading or other similar mechanism the tightening of which permits movement of the spacer 300 from a collapsed position to an expanded position.

The upper portion of first leg 310 and the upper portion of second leg 320 are each coupled to a superior bearing surface 390 via cross pins 350 and 360 respectively. Similarly, the lower portion of third leg 330 and the lower portion of fourth leg 340 are each coupled to an inferior surface 380 via cross pins 375 and 370 respectively.

The superior and inferior bearing surfaces 390 and 380 are configured to bear against an inferior surface of a superior spinous process SP and the superior surface of the inferior spinous process SP, respectively. Bearing surfaces 380 and 390 may be constructed of nearly any material that is able to take on the general shape of the bearing surfaces 380 and 390 and withstand their normal operating conditions.

Figure 12:
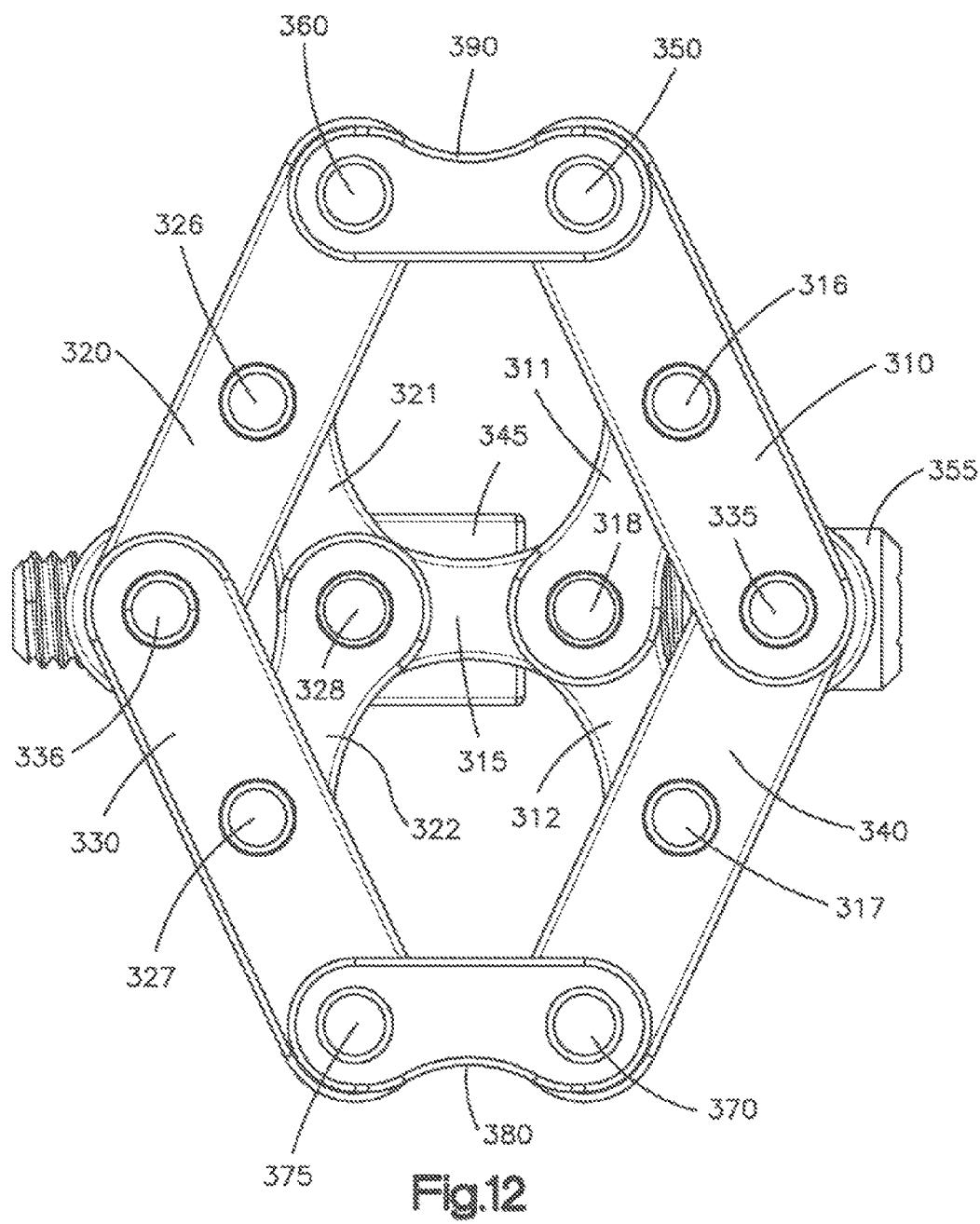
FIG. 12 illustrates a front elevational view of an expandable interspinous process spacer according to a third preferred embodiment of the present invention in an expanded state.
Figure 13:
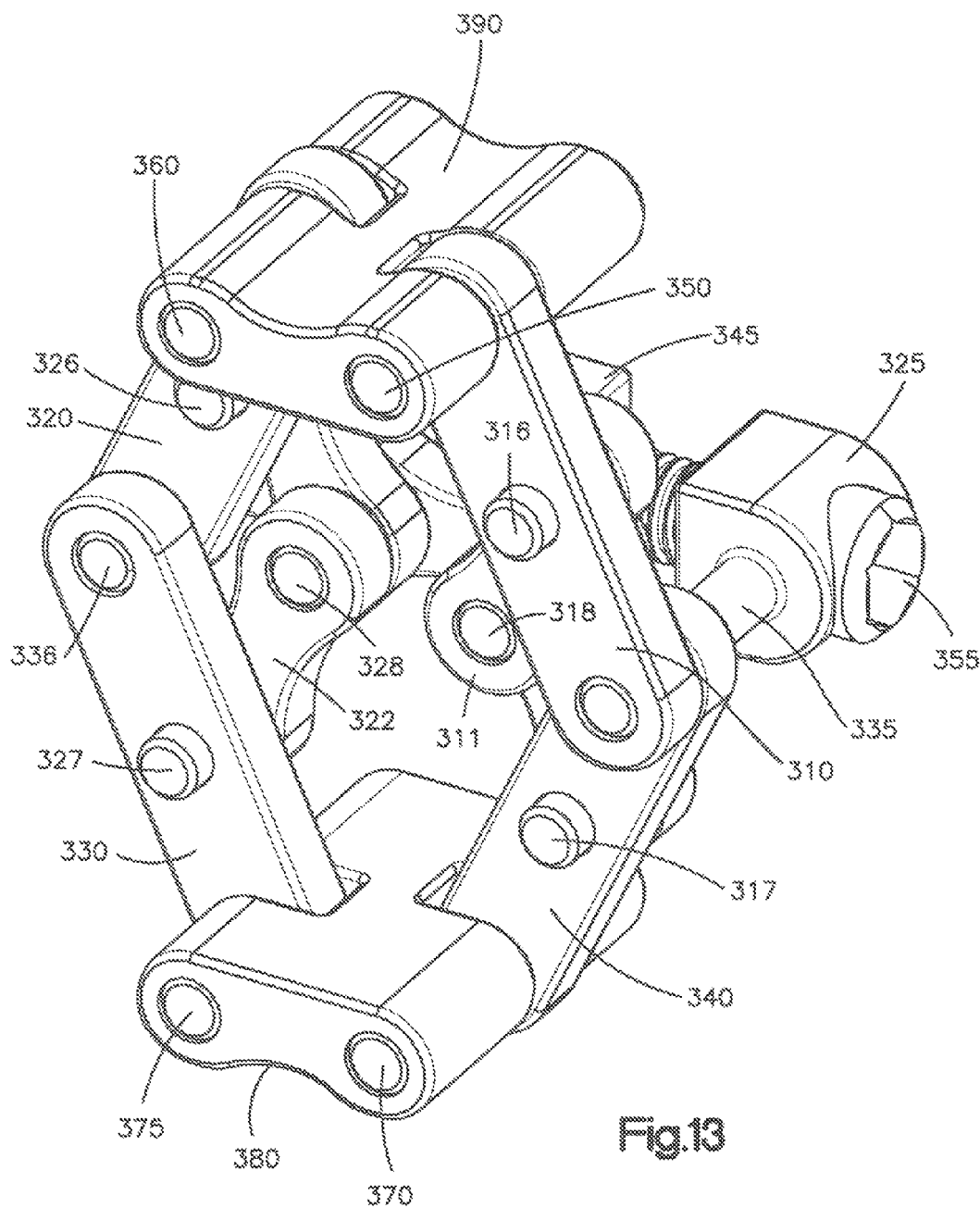
FIG. 13 illustrates a side perspective view of the expandable interspinous process spacer shown in FIG. 12.
Figure 14:
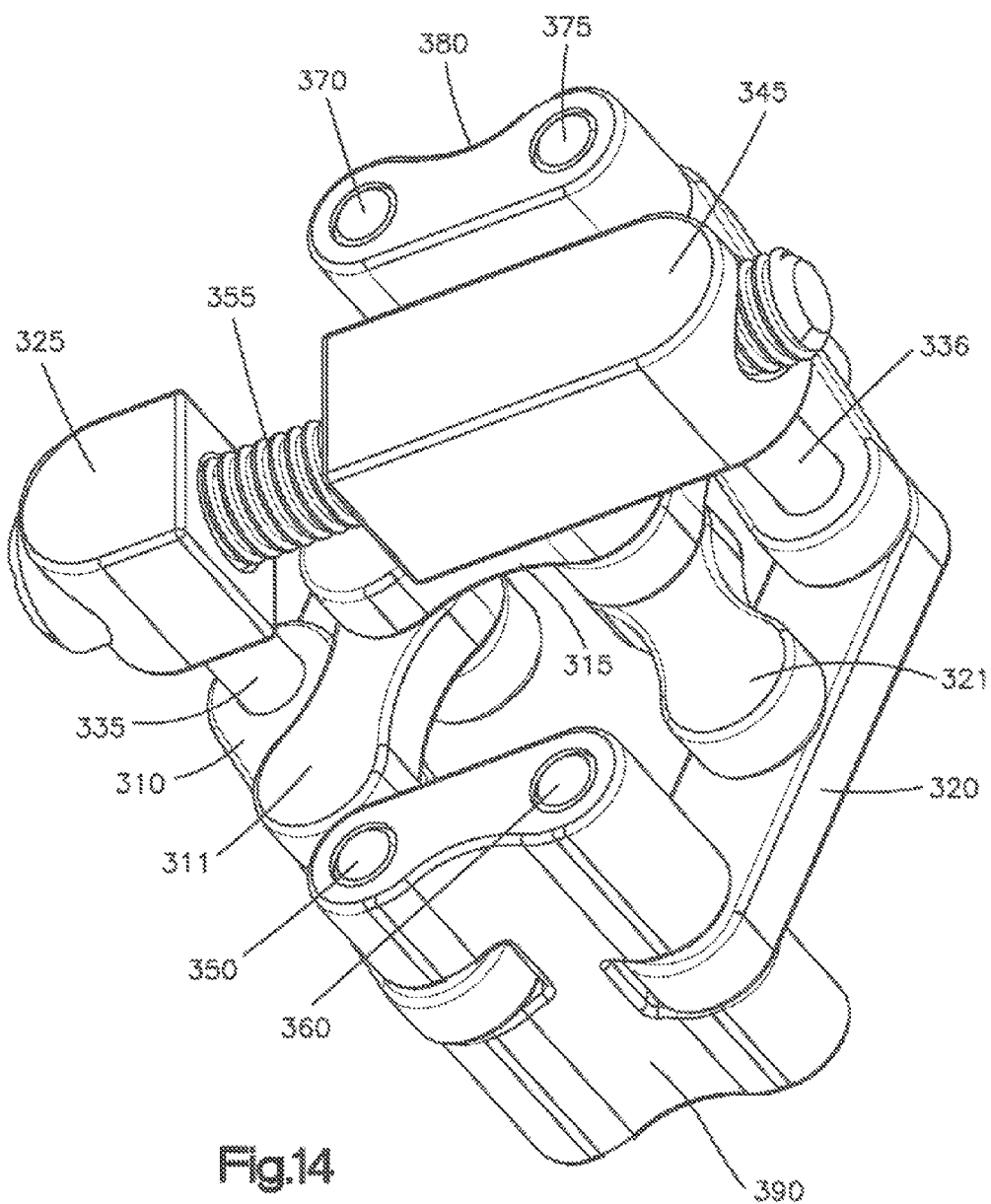
FIG. 14 illustrates a side perspective view of the expandable interspinous process spacer shown in FIG. 12.
Figure 15:
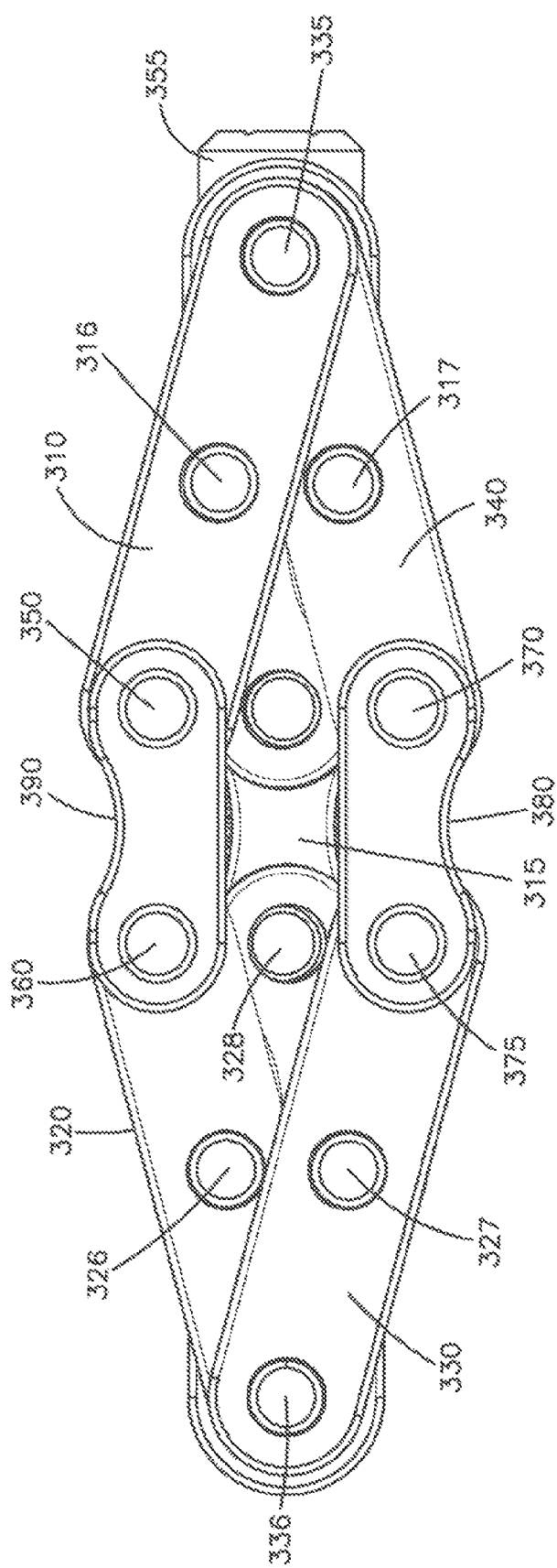
FIG. 15 illustrates a side elevational view of the expandable interspinous process spacer shown in FIG. 12 in a collapsed state.

The interspinous process spacer 300 of the third preferred embodiment is adjustable from a non-expanded, collapsed configuration as shown in FIGS. 15-16 to an expanded deployed configuration as shown in FIGS. 12-14. Spacer 300 may be adapted to the patient's anatomy during implantation by adjusting the height of spacer 300. Moreover, as will be appreciated by one of ordinary skill in the art, the angulation of the spacer 300 may be adjusted by independently adjusting the anterior and posterior ends of spacer 300. FIG. 17 illustrates a preferred use of the spacer 300 implanted in the spine, between spinous processes SP of adjacent vertebrae.

One exemplary surgical technique for implanting spacer 300 is described below, however, those skilled in the art will appreciate that spacer 300 may be implanted utilizing numerous techniques and/or surgical steps that would be apparent to one having ordinary skill in the art, following a review of the disclosure herein.

In use, the interspinous process spacer 300 is implanted to treat patients with spinal stenosis. A lateral or medial lateral approach corridor is provided and the interspinous ligament is preferably pierced or partially removed although the interspinous ligament may be left intact. The implant 300 is preferably inserted laterally through the approach corridor in a collapsed configuration and is implanted between the adjacent spinous processes. Once the implant 300 is positioned, an instrument is introduced through the corridor and coupled to an instrument engagement feature on the head of the expansion screw 355. The expansion screw 355 is actuated, preferably through rotation, causing the threaded shaft of the expansion screw 355 to interact with the screw hole of the second plate 345 and thereby drawing the first plate 355 and the second plate 345 toward each other toward the center of the implant 300.

As the second plate 345 and the first plate 355 are drawn towards each other, the bottom end of the second leg 320 and the top end of the third leg 330 as well as the bottom end of the first leg 310 and the top end of the fourth leg 340 move towards the center of the implant 300. Additionally, the drawing together of the first and second plates 355 and 345 and the resultant movement of the legs forces the superior bearing surface 390 and the inferior bearing surface 380 to be distracted from one another and the height of the implant 300 to increase.

Once the screw 355 had been tightened, the implant 300 is prevented from collapsing due to interference created between the threading on the screw 355, and the screw hole on the second plate 345 which is preferably threaded. Alternately or in addition thereto, the screw 355 may be locked after the expansion of the implant, e.g., by placing a nut on the distal end of the screw opposite the second plate 345. Once the desired spacing between the adjacent spinous processes has been achieved, the instrument is removed and the wound is closed. The implant 300 is not limited to lateral or minimally invasive insertions and may be implanted from a posterior approach or a posterior-lateral approach and/or through a mini-open or open incision in a patient.

One having ordinary skill in the art will recognize that the various engagement mechanisms described for the preferred embodiments of the interspinous spacer assemblies may be adapted and interchanged between the interspinous spacer assemblies of preferred embodiments, without significantly impacting the structure and operation of the implants.

Those skilled in the art will recognize that the method and system of the present invention has many applications, may be implemented in many manners and, as such is not to be limited by the foregoing embodiments and examples. Any number of the features of the different embodiments described herein may be combined into one single embodiment and alternate embodiments having fewer than or more than all of the features herein described are possible. Functionality may also be, in whole or in part, distributed among multiple components, in manners now known or to become known. Moreover, the scope of the present invention covers conventionally known and features of those variations and modifications through the components described herein as would be understood by those skilled in the art. It is the intention, therefore, to be limited only as indicated by the scope of the claims appended hereto.

It is also to be understood that the following claims are intended to cover all of the generic and specific features of the invention herein described and all statements of the scope of the invention, which, as a matter of language, might be said to fall therebetween.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. An expandable interspinous process spacer implant for treating spinal stenosis in the spine, the implant having a first end and a second end and a length therebetween, a proximal side and a distal side and a width therebetween, and an expandable height, the implant comprising:
    a first pair of legs, each leg having a first and second end, the first pair of legs pivotally joined with each other, wherein the first pair of legs are pivotally joined by a first connector that is pivotally connected to each of the first pair of legs;
    a second pair of legs, each leg having a first and second end, the second pair of legs pivotally joined with each other;
    a first plate having a first plate hole configured to receive a head portion of a fastener, the first plate coupled to the first pair of legs;
    a second plate having a second plate hole configured to receive a shaft portion of the fastener, the second plate coupled to the second pair of legs;
    a superior bearing surface connecting the first end of one of the first pair of legs with the first end of one of the second pair of legs; and
    an inferior bearing surface connecting the second end of one of the first pair of legs with the second end of one of the second pair of legs;
    wherein decreasing the distance between the first plate and the second plate causes an increase in vertical distance between the two bearing surfaces.

2. The implant of claim 1 wherein the first plate hole is unthreaded and the second plate hole is threaded.

3. The implant of claim 1 wherein the first plate hole and the second plate hole are threaded.

4. The implant of claim 1 wherein the fastener is an expansion screw.

5. The implant of claim 1 wherein the implant further comprises an engagement mechanism to engage the spinous process of the inferior or superior vertebral body.

6. The implant of claim 1, wherein the second pair of legs are pivotally joined by a second connector that is pivotally connected to each of the second pair of legs.

7. The implant of claim 6, wherein the first connector and the second connector are pivotally joined to an expander.

8. The implant of claim 1, wherein the fastener is a threaded expansion screw.

9. The implant of claim 1, wherein the superior bearing surface and the inferior bearing surface are configured to bear against an inferior surface of a superior spinous process SP and a superior surface of an inferior spinous process SP, respectively.

10. The implant of claim 1, wherein first pair of legs includes a first leg member pivotally coupled to a second leg member, the first leg member coupled to the superior bearing surface and the second leg member coupled to the inferior bearing surface.

11. The implant of claim 10, wherein the first leg member and the second leg member are coupled at a cross pin.

12. The implant of claim 11, wherein the first plate is coupled to the first pair of legs at the cross pin.

13. The implant of claim 10, wherein the first pair of legs are pivotally joined by a first connector that is pivotally connected to each of the first leg member and the second leg member at corresponding first and second fulcrum pins.

14. The implant of claim 13, wherein the first connector includes an upper connector member pivotally joined to a lower connector member, the upper connector member coupled to the first leg member at the first fulcrum pin and the lower connector member coupled to the second leg member at the second fulcrum pin.

15. The implant of claim 1, wherein the second pair of legs includes a third leg member pivotally coupled to a fourth leg member, the third leg member coupled to the superior bearing surface and the second leg member coupled to the inferior bearing surface.

16. The implant of claim 15, wherein the third leg member and the fourth leg member are coupled at a cross pin.

17. The implant of claim 16, wherein the second plate is coupled to the third leg member and the fourth leg member at the cross pin.

18. The implant of claim 15, wherein the second pair of legs are pivotally joined by a second connector that is pivotally connected to each of the third leg member and the fourth leg member at corresponding third and fourth fulcrum pins.

19. The implant of claim 18, wherein the second connector includes an upper connector member pivotally joined to a lower connector member, the upper connector member coupled to the third leg member at the third fulcrum pin and the lower connector member coupled to the fourth leg member at the fourth fulcrum pin.

20. An expandable interspinous process spacer implant for treating spinal stenosis in the spine, the implant having a first end and a second end and a length therebetween, a proximal side and a distal side and a width therebetween, and an expandable height, the implant comprising:
- a first pair of legs, each leg having a first and second end, the first pair of legs pivotally joined with each other;
- a second pair of legs, each leg having a first and second end, the second pair of legs pivotally joined with each other;
- a first plate having a first plate hole configured to receive a head portion of a fastener, the first plate coupled to the first pair of legs;
- a second plate having a second plate hole configured to receive a shaft portion of the fastener, the second plate coupled to the second pair of legs;
- a superior bearing surface connecting the first end of one of the first pair of legs with the first end of one of the second pair of legs; and
- an inferior bearing surface connecting the second end of one of the first pair of legs with the second end of one of the second pair of legs;
- wherein decreasing the distance between the first plate and the second plate causes an increase in vertical distance between the two bearing surfaces,
- wherein the fastener is a threaded expansion screw.

21. An expandable interspinous process spacer implant for treating spinal stenosis in the spine, the implant having a first end and a second end and a length therebetween, a proximal side and a distal side and a width therebetween, and an expandable height, the implant comprising:
- a first pair of legs, each leg having a first and second end, the first pair of legs pivotally joined with each other;
- a second pair of legs, each leg having a first and second end, the second pair of legs pivotally joined with each other;
- a first plate having a first plate hole configured to receive a head portion of a fastener, the first plate coupled to the first pair of legs;
- a second plate having a second plate hole configured to receive a shaft portion of the fastener, the second plate coupled to the second pair of legs;
- a superior bearing surface connecting the first end of one of the first pair of legs with the first end of one of the second pair of legs; and
- an inferior bearing surface connecting the second end of one of the first pair of legs with the second end of one of the second pair of legs;
- wherein the superior bearing surface and the inferior bearing surface are configured to bear against an inferior surface of a superior spinous process SP and a superior surface of an inferior spinous process SP, respectively,
- wherein decreasing the distance between the first plate and the second plate causes an increase in vertical distance between the two bearing surfaces.

* * * * *